United States Patent [19]
Greve et al.

[11] Patent Number: 6,096,862
[45] Date of Patent: *Aug. 1, 2000

[54] MULTIMERIC ANTIVIRAL AGENT

[75] Inventors: Jeffrey M. Greve, Branford; Alan McClelland, Old Saybrook, both of Conn.

[73] Assignee: Bayer Corporation, Pittsburgh, Pa.

[*] Notice: This patent is subject to a terminal disclaimer.

[21] Appl. No.: 08/318,039

[22] Filed: Oct. 4, 1994

Related U.S. Application Data

[63] Continuation of application No. 08/159,076, Nov. 29, 1993, abandoned, which is a continuation of application No. 07/977,589, Nov. 17, 1992, abandoned, which is a continuation of application No. 07/556,238, Jul. 20, 1990, abandoned.

[51] Int. Cl.$^7$ ..................................................... C07K 5/00
[52] U.S. Cl. .......................... 530/324; 530/325; 530/326; 530/327; 530/328; 530/329; 530/350; 530/395; 530/402; 530/345; 514/12; 514/13; 514/14; 514/15; 514/16; 514/17; 424/185.1
[58] Field of Search ..................................... 530/300, 350, 530/395, 830, 868, 402, 403, 324, 325, 326, 327, 328, 329, 345; 514/2, 8, 12–17; 435/7.1; 436/501; 424/185.1

[56] References Cited

U.S. PATENT DOCUMENTS

| | | |
|---|---|---|
| 4,171,365 | 10/1979 | Diana et al. . |
| 4,209,526 | 6/1980 | Diana et al. . |
| 4,232,161 | 11/1980 | Diana et al. . |
| 4,234,725 | 11/1980 | Diana et al. . |
| 4,261,928 | 4/1981 | Diana et al. . |
| 4,372,976 | 2/1983 | Diana . |
| 4,427,653 | 1/1984 | Springer . |
| 4,451,476 | 5/1984 | Diana . |
| 4,843,087 | 6/1989 | Diana . |
| 4,956,281 | 9/1990 | Wallner et al. . |
| 5,081,228 | 1/1992 | Dower et al. . |
| 5,109,123 | 4/1992 | Reinherz et al. . |
| 5,179,017 | 1/1993 | Axel et al. . |
| 5,235,049 | 8/1993 | McClelland et al. . |
| 5,240,694 | 8/1993 | Gwaltney, Jr. . |
| 5,284,931 | 2/1994 | Springer et al. . |
| 5,304,636 | 4/1994 | Blaas et al. . |
| 5,324,510 | 6/1994 | Wegner et al. . |
| 5,340,800 | 8/1994 | Liu et al. . |
| 5,349,053 | 9/1994 | Landolfi . |
| 5,359,046 | 10/1994 | Capon et al. . |
| 5,372,933 | 12/1994 | Zamarron et al. . |
| 5,395,929 | 3/1995 | Corbi et al. . |
| 5,422,097 | 6/1995 | Gwaltney . |
| 5,472,849 | 12/1995 | Rothlein et al. . |
| 5,475,091 | 12/1995 | Springer et al. . |
| 5,525,487 | 6/1996 | Gallatin et al. . |
| 5,532,127 | 7/1996 | Gallatin et al. . |
| 5,580,969 | 12/1996 | Hoke et al. . |
| 5,589,453 | 12/1996 | Greve . |
| 5,597,567 | 1/1997 | Whitcup et al. . |
| 5,603,932 | 2/1997 | Blaas et al. . |
| 5,612,216 | 3/1997 | Springer et al. . |
| 5,663,293 | 9/1997 | Gallatin et al. . |
| 5,674,982 | 10/1997 | Greve et al. . |
| 5,686,581 | 11/1997 | Greve et al. . |
| 5,686,582 | 11/1997 | Greve et al. . |
| 5,712,245 | 1/1998 | Blaas et al. . |
| 5,730,983 | 3/1998 | Wegner et al. . |
| 5,821,341 | 10/1998 | McClelland et al. . |
| 5,831,036 | 11/1998 | Springer et al. . |
| 5,849,699 | 12/1998 | McClelland et al. . |
| 5,871,733 | 2/1999 | Greve et al. . |

FOREIGN PATENT DOCUMENTS

| | | |
|---|---|---|
| 14630/88 | 10/1988 | Australia . |
| 1551888 | 11/1988 | Australia . |
| 2633288 | 5/1989 | Australia . |
| 623105 | 6/1989 | Australia . |
| 48767/90 | 2/1990 | Australia . |
| 637324 | 3/1990 | Australia . |
| 5129990 | 9/1990 | Australia . |
| 623105 | 5/1992 | Australia . |
| 637324 | 5/1993 | Australia . |
| 641134 | 9/1993 | Australia . |
| 652567 | 9/1994 | Australia . |
| 675441 | 2/1997 | Australia . |
| 1339193 | 8/1997 | Canada . |
| 0169146A3 | 1/1986 | European Pat. Off. . |
| 0169729A2 | 1/1986 | European Pat. Off. . |
| 0192175A2 | 8/1986 | European Pat. Off. . |
| 0207453A2 | 1/1987 | European Pat. Off. . |
| 0227604A2 | 7/1987 | European Pat. Off. . |
| 0261403A2 | 3/1988 | European Pat. Off. . |
| 0280578A2 | 8/1988 | European Pat. Off. . |
| 0287076 | 10/1988 | European Pat. Off. . |
| 0287076B1 | 10/1988 | European Pat. Off. . |
| 0289949A2 | 11/1988 | European Pat. Off. . |

(List continued on next page.)

OTHER PUBLICATIONS

Abraham, G. and Colonno, R. J., "Many Rhinovirus Serotypes Share the Same Cellular Receptor", J. Virol. 51:340–345 (1984).

Anasetti et al., "Activation of Natural Killer Cells by LFA–3 Binding to CD2", 4$^{th}$ International Conference on Human Leukocyte Differentiation Antigens, Vienna, Austria, Feb. 21–25, 1989, Tissue Antigens (1989) 33(2), 73.

(List continued on next page.)

Primary Examiner—Christina Y. Chan
Assistant Examiner—Marianne DiBrino

[57] ABSTRACT

Multimeric antiviral agents comprising two or more monomers selected from the group consisting of monomers of transmembrane intracellular adhesion molecule-1 (tmICAM-1) and truncated intercellular adhesion molecule-1 (tICAMs), with the proviso that when said multimer is a dimer said monomers cannot both be tmICAM-1, wherein each of said monomers comprises the human rhinovirus (HRV) binding site and retains the ability to bind to HRV and reduce infectivity thereof, and wherein said multimeric antiviral agent mimics the multimeric configuration of tmICAM-1 and exhibits enhanced binding to said HRV relative to at least one of the constituent monomers.

10 Claims, No Drawings

FOREIGN PATENT DOCUMENTS

| | | |
|---|---|---|
| 0314863A2 | 5/1989 | European Pat. Off. . |
| 0319815A2 | 6/1989 | European Pat. Off. . |
| 0380068A1 | 1/1990 | European Pat. Off. . |
| 0362526A2 | 4/1990 | European Pat. Off. . |
| 0362531A1 | 4/1990 | European Pat. Off. . |
| 0364690A2 | 4/1990 | European Pat. Off. . |
| 0365837A2 | 5/1990 | European Pat. Off. . |
| 0379904A1 | 8/1990 | European Pat. Off. . |
| 0387668A1 | 9/1990 | European Pat. Off. . |
| 0387701B1 | 9/1990 | European Pat. Off. . |
| 0391088A2 | 10/1990 | European Pat. Off. . |
| 0459577A2 | 12/1991 | European Pat. Off. . |
| 0468257 | 1/1992 | European Pat. Off. . |
| 0510483 | 10/1992 | European Pat. Off. . |
| 0566554 | 10/1993 | European Pat. Off. . |
| 0319815 | 8/1994 | European Pat. Off. . |
| 0379904 | 5/1996 | European Pat. Off. . |
| 0488061 | 11/1998 | European Pat. Off. . |
| 100601 | 1/1998 | Finland . |
| 3712678A1 | 10/1988 | Germany . |
| 74144 | 7/1997 | Ireland . |
| 91454 | 8/1995 | Israel . |
| 230474 | 8/1989 | New Zealand . |
| 232203 | 1/1990 | New Zealand . |
| 92920 | 7/1990 | Portugal . |
| 91570 | 11/1994 | Portugal . |
| 202435 | 6/1999 | Rep. of Korea . |
| 90/0469 | 10/1990 | Saudi Arabia . |
| 900469 | 10/1990 | South Africa . |
| 52785 | 11/1991 | Taiwan . |
| 52785 | 3/1992 | Taiwan . |
| 2022826 | 12/1979 | United Kingdom . |
| WO 88/06592 | 9/1988 | WIPO . |
| WO 89/10938 | 11/1989 | WIPO . |
| WO 90/03400 | 4/1990 | WIPO . |
| WO 90/10646 | 9/1990 | WIPO . |
| WO 90/10652 | 9/1990 | WIPO . |
| WO 90/13316 | 11/1990 | WIPO . |
| WO 91/16927 | 11/1991 | WIPO . |
| WO 91/16928 | 11/1991 | WIPO . |
| WO 91/18010 | 11/1991 | WIPO . |
| WO 91/18011 | 11/1991 | WIPO . |
| 9201049 | 1/1992 | WIPO . |
| 9206119 | 4/1992 | WIPO . |
| 9212994 | 8/1992 | WIPO . |
| 9306842 | 4/1993 | WIPO . |
| 9306850 | 4/1993 | WIPO . |
| 9313210 | 7/1993 | WIPO . |
| 9401553 | 1/1994 | WIPO . |
| 9411400 | 5/1994 | WIPO . |
| 9527736 | 10/1995 | WIPO . |
| 9528170 | 10/1995 | WIPO . |
| 9606622 | 3/1996 | WIPO . |
| 9627292 | 9/1996 | WIPO . |
| 9634015 | 10/1996 | WIPO . |

OTHER PUBLICATIONS

Argenbright et al., "Monoclonal Antibodies to the Leukocyte Membrane CD18 Glycoprotein Complex and to Intercellular Adhesion Molecule–1 Inhibit Leukocyte–Endothelial Adhesion in Rabbits", J. Leukoc. Biol. 49:253–257 (1991).

Argenbright, L. W. and Barton, R. W., "Interactions of Leukocyte Integrins with Intercellular Adhesion Molecule–1 in the Production of Inflammatory Vascular Injury In Vivo: the Shwartzman Reaction Revisited", J. Clin. Invest. 89(1):259–272 (1992).

Badger et. al., "Structure Analysis of a Series of Antiviral Agents Complexed with Human Rhinovirus 14", PNAS 85:3304–3308 (1988).

Bangham, C. R. M. and McMichael, A. J., "Nosing ahead in the cold war" Nature 334:16 (1990).

Bebbington, C. R., and Hentschel, C. C. G. "The use of vectors based on gene amplification for the expression of cloned genes in mammalian cells" DNA Cloning 3:163–186 (1987).

Blann, A. D., "Cell Hybrids: an important new source o antibody production" Med. Lab. Sci. 36:329–338 (1979).

Bock et al., "Characterization of soluble forms of NCAM", FEBS Lett 225(1,2):33–36 (1987).

Bowie et al., "Deciphering the Message in Protein Sequences: Tolerance to Amino Acid Substitutions", Science 247:1306–1310 (1990).

Campbell, B. A. and Cords, C. E., "Monoclonal Antibodies That Inhibit Attachment of Group B Coxsackieviruses", J. Virol. 48(2):561–564 (1983).

Capon et al., "Designing CD4 immunoadhesins for AIDS therapy", Nature 337:525–531 (1989).

Cate et al., "Isolation of the Bovine and Human Genes for Müllerian Inhibiting Substance and Expression of the Human Gene in Animal Cells", Cell 45:685–698 (1986).

Cole et al., "Topographic Localization of the Heparin–binding Domain of the Neural Cell Adhesion Molecule N–CAM", J. Cell Biol. 103:1739–1744 (1986).

Colonno et al., "Isolation of a Monoclonal Antibody that Blocks Attachment of the Major Group of Human Rhinoviruses", J. Virology 57:7–12 (1986).

Colonno, R. J. and Tomassini, J. E., "Viral Receptors: A Novel Approach For The Prevention Of Human Rhinovirus Infection", in *Medical Virology VI*, de la Maza, L. M. and E. M. Peterson, eds. (Elsevier, New York, 1987) 331–351.

Cooper, G.M., "Cellular Transforming Genes", Science 217: 801–806 (1982).

Couch, R.B., "Rhinoviruses", *Virology*, Second Edition, edited by B. N. Fields, D. M. Knipe et al. Raven Press, Ltd., New York, 607–629 (1990).

Couch et al., "Effect of Route Inoculation on Experimental Respiratory Viral Disease in Volunteers and Evidence for Airborne Transmission", Bacteriol. Rev. 30:517–529 (1966).

Creighton, T.E., *Proteins* by W. H. Freeman and Company, New York, 33–34 (1984).

Crump et al., "In Vitro Inhibitory Activity of Soluble ICAM–1 for the Numbered Serotypes of Human Rhinovirus", Antiviral Chemistry and Chemother. 4(6):323–327 (1993).

Cunningham et al., "Neural Cell Adhesion Molecule: Structure, Immunoglobulin–Like Domains, Cell Surface Modulation, and Alternative RNA Splicing", Science 236:799–806 (1987).

Cybulsky, M. I. and Gimbrone, Jr., M. A., "Endothelial Expression of a Mononuclear Leukocyte Adhesion Molecule During Atherogenesis", Science 251:788–791 (1991).

D'Alessio et al., "Short–Duration Exposure and the Transmission of Rhinoviral Colds", J. Inf. Dis. 150(2):189–193 (1984).

Deen et al., "A Soluble Form of CD4 (T4) Protein Inhibits AIDS Virus Infection", Nature 331:82–86 (1988).

Dick, E.C., "Experimental Infection of Chimpanzees with Human Rhinovirus Types 14 and 43", Proceedings Of The Society For Experimental Biology And Medicine 127:1079–1081 (1968).

Dochez et al., "Studies in the Common Cold. IV. Experimental Transmission of the Common Cold to Anthropoid Apes and Human Beings by Means of a Filtrable Agent", J. Exp. Med. 52:701–716 (1930).

Douglas et al., "Prophylactic Efficacy of Intranasal Alpha 2–Interferon Against Rhinovirus Infections in the Family Setting", The New England J. of Med. 314:65–70 (1986).

Douglas, R. G., "Pathogenesis of Rhinovirus Common Colds in Human Volunteers", Annals of Otology, Rhinology and Laryngology 79:563–571 (1970).

Dustin et al., "Induction by IL 1 and Inteferon–γ: Tissue Distribution, Biochemistry, and Function of a Natural Adherence Molecule (ICAM–1)", J. Immunol. 137(1):245–254 (1986).

Dustin et al., "Supergene Families Meet in the Immune System" Immunology Today, 9(7 and 8):213–215 (1988).

Dustin et al., "Correlation of CD2 Binding and Functional Properties of Multimeric and Monomeric Lymphocyte Function–Associated Antigen 3", J. Exp. Med. 169:503–517 (1989).

Ey, P.L., et. al.,"Isolation of Pure IgG1, IgG2a, and IgG2b Immunoglobulins from Mouse Serum Using Protein A—Sepharose", Immunochemistry 15:429–436 (1978).

Fisher et al., "HIV Infection is Blocked in vitro by Recombinant Soluble CD4", Nature 331:76–78 (1988).

Fox et al., "Prevention of a Rhinovirus and Poliovirus Uncoating by WIN 51711, a New Antiviral Drug", Antimicrob. Ag. and Chemotherapy 30:110–116 (1986).

Galfrey et. al., "Antibodies to Major Histocompatibility Antigens Produced by Hybrid Cell Lines", Nature 266:550–552 (1977).

Gething, M.J. and Sambrook, J., "Construction of Influenza Haemagglutinin Genes that Code for Intracellular and Secreted Forms of the Protein" Nature 300:598–603 (1982).

Ginsberg et al., "Inhibition of Fibronectin Binding to Platelets by Proteolytic Fragments and Synthetic Peptides Which Support Fibroblast Adhesion", J. Biol. Chem. 260(7):3931–3936 (1985).

Giranda et al., "Modelling of the Human Intercellular Adhesion Molecule–1, the Human Rhinovirus Major Group Receptor" Proteins: Structure, Function, and Genetics, 7:227–233 (1990).

Gough, N., "Putting A Stop To An Immunoglobulin Message", Trends Genet. 3(9):238–240 (1987).

Gower et al., "Alternative Splicing Generates a Secreted Form of N–CAM in Muscle and Brain", Cell 55:955–964 (1988).

Graham, F.L., and Van der Eb, A. J., "A New Technique for the Assay of Infectivity of Human Adenovirus 5 DNA", Virology 52: 456–467 (1973).

Green et al., "Immunogenic Structure of the Influenza Virus Hemagglutinin", Cell 28:477–487 (1982).

Greve et al., "The Major Human Rhinovirus Receptor Is ICAM–1", Cell 56:839–847 (1989).

Greve et al. "Mechanisms of Receptor–Mediated Rhinovirus Neutralization Defined by Two Soluble Forms of ICAM–1", J. Virology 65:6015–6023 (1991).

Gross–Bellard et al., "Isolation of High–Molecular–Weight DNA from Mammalian Cells", Eur. J. Biochem. 36:32–38 (1973).

Güssow, D. and Ploegh, H., "Soluble class I antigens: a conundrum with no solution?", Immunology Today 8(7, 8):220–222 (1987).

Gwaltney et al., *Diagnostic Procedures for Viral, Rickettsial and Chlamydial Infections*, N. J. Schmidt and R. W. Evans, Eds, 6th edition. p. 603, Am Pub. Health. Assoc., Washington D.C. (1989).

Halperin et al., "Exacerbations of Asthma in Adults During Experimental Rhinovirus Infection", Am. Rev. Respir. Dis. 132:976–980 (1985).

Hamparian et al., "A Collaborative Report: Rhinoviruses—Extension of the Numbering System from 89 to 100", Virology 159:191–192 (1987).

Hardy et al., "Intranasal Drug Delivery by Spray and Drops", J. Pharm. Pharmacol. 37:294–297 (1985).

Harning et al., "Serum Levels of Circulating Intercellular Adhesion Molecule 1 in Human Malignant Melanoma", Cancer Res. 51(8):5003–5005 (1991).

Hayden et al., "Safety and Efficacy of Intranasal Pirodavir (R77975) in Experimental Rhinovirus Infection", Antimicrob. Agents Chemother. 36(4):727–732 (1992).

Hayden et al., "Prevention of Natural Colds by Contact Prophylaxis with Intranasal Alpha2–Interferon", The New England Journal of Medicine, 314(2):71–75 (1986).

Hayden et al., "Modification of Experimental Rhinovirus Colds by Receptor Blockade" Antiviral Research 9:233–247 (1988).

Helenius, A. and Von Bonsdorff, C. H., "Semliki Forest Virus Membrane Proteins, Preparation and Characterization of Spike Complexes Soluble in Detergent–Free Medium" Biochimica et Biophysica Acta 436:895–899 (1976).

Hendley et al., "Relation Between Naturally acquired Immunity and Infectivity of Two Rhinoviruses in Volunteers", J. Inf. Dis. 125:243–248 (1972).

Holland, J. J. and McLaren, L. C., "The mammalian cell–virus relationship. II. Absorption, Reception and Eclipse of Poliovirus by HeLa Cells", J. Exp. Med. 109:487–504 (1959).

Holland, J. J., "Receptor affinities as Major Determinants of Enterovirus Tissue Tropisms in Humans", Virology 15:312–326, 1961.

Horton et al., "Gene Splicing by Overlap Extension: Tailor–Made Genes Using the Polyerase Chain Reaction", Bio-Techniques 8(5):528–535 (1990).

Hussey et. al., "A Soluble CD4 Protein Selectively Inhibits HIV Replication and Syncytium Formation" Nature, 331:78–81 (1988).

Illum, L., "The Nasal Delivery of Peptides and Proteins", Trends in Biotech. 9:284–289 (1991).

Johnston et al., "Viruses as Precipitants of Asthma Symptoms. III. Rhinoviruses: Molecular Biology and Prospects for Future Intervention", Clin. Exp. Allergy, 23:237 (1993).

Johnston et al., "Viral Infections in Exacerbations in School Children with Cough or Wheeze: A Longitudinal Study", Am. Rev. Resp. Dis., 145:A546 (1992).

Kamarck, M. E., and Ruddle, F. H., "Somatic Cell Genetics and the Human Gene Map", Chapter 105 in *Handbook of Experimental Immunology in Four Volumes, vol 3: Genetics and Molecular Immunology*, D. M. Weir, ed. (Blackwell Scientific Publications, Boston, MA, 1986).

Katz et al., "Chromosome Mapping of Cell Membrane Antigens Expressed on Activated B Cells", Eur. J. Immunol., 15:103–106 (1985).

Kavenoff, R., and Zimm, B. H., "Chromosome–Sized DNA Molecules from Drosophila", Chromosoma (Berl.) 41:1–27 (1973).

Kühn et al., "Gene Transfer, Expression, and Molecular Cloning of the Human Transferrin Receptor Gene", Cell 37:95–103 (1984).

Lebman et al., "A Monoclonal Antibody that Detects Expression of Transferrin Receptor in Human Erythroid Precursor Cells", Blood 59(3):671–678 (1982).

Lemanske et al., "Rhinovirus Upper Respiratory Infection Increases Airway Hyperreactivity and Late Asthmatic Reactions", J. Clin. Invest. 83:1–10 (1989).

Littlefield, J.W., "Selection of Hybrids from Matings of Fibroblasts in vitro and Their Presumed Recombinants", Science 145:709–710 (1964).

Lonberg–Holm et al., "Unrelated Animal Viruses Share Receptor", Nature 259:679–681 (1976).

Margulies, D. H., et. al., "Engineering Soluble Major Histocompatibility Molecules: Why and How", Immunol. Res. 6: 101–116 (1987).

Marlin, S.D. and Springer, T. A., "Purified Intercellular Adhesion Molecule–1 (ICAM–1) Is a Ligand for Lymphocyte Function–Associated Antigen 1 (LFA–1)", Cell 51:813–819 (1987).

Marlin et al., "A Soluble Form of Intercellular Adhesion Molecule–1 Inhibits Rhinovirus Infection", Nature 344:70–72 (1990).

Marsh et al., "Antibody–toxin Conjugation", *Immunotoxins* by Kluwer Academic Publishers, Boston, Dordrecht, Lancaster 213–237 (1988).

Marsh et al., "Interactions of Semliki Forest Virus Spike Glycoprotein Rosettes and Vesicle with Cultures Cells", J. Cell Biology 96:455–461 (1983).

McClelland et al., "Identification of Monoclonal Antibody Epitopes and Critical Residues for Rhinovirus in Domain 1 of ICAM–1", PNAS 88(18):7993–7997 (1991).

McClelland et al., "Transfectant cell lines which express the major human rhinovirus receptor, their preparation, and their uses", Immuno. 112:117179 (1990).

McCray, J. and Werner, G., "Different Rhinovirus Serotypes Neutralized by Antipeptide Antibodies", Nature 329:736–738 (1987).

Medical Microbiology: "An Introduction to Infectious Diseases", 2nd ed., J.C. Sherris, ed. (Elsevier Science Publishing Co., Inc., N.Y. 1990) pp. 514–515.

Medrano, L. and Green, H., "Picornavirus Receptors and Picornavirus Multiplication in Human–Mouse Hybrid Cell Lines", Virology 54:515–524 (1973).

Melchers et al. *Lymphocyte Hybridomas*, vol. 81 of Current Topics in Microbiology and Immunology, W. Arber, W. Henle, P.H. Hofschneider, J.H. Humphrey, J. Klein, P. Koldovsky, H. Koprowski, O. Maaloe, F. Melchers, R. Rott, H.G. Schweiger, L. Syrucek, P.K. Vogt, eds (Springer Verlang, New York, 1978).

Mendelsohn et al., "Transformation of a Human Poliovirus Receptor Gene into Mouse Cells", PNAS 83:7845–7849 (1986).

Minor, P.D., "Growth, Assay and Purification of Picornaviruses", in *Virology: A Practical Approach*, B.W.J. Mahy, ed. (IRL Press Limited, Oxford, England), 25–41 (1985).

Minor et al., "Monoclonal antibodies which block cellular receptors of poliovirus", Virus Research 1:203–212 (1984).

Morein, B., "Potentiation of the Immune Response by Immunization with Antigens in Defined Multimeric Physical Forms", Veterinary Immunology and Immunopathology 17:153–159 (1987).

Niman et al., "Anti–peptide antibodies detect oncogene–related proteins in urine", PNAS 82:7924–7928 (1985).

Nobis et al., "Production of a Monoclonal Antibody against an Epitope on HeLa Cells that Is the Functional Poliovirus Binding Site", J. Gen. Virol. 66:2563–2569 (1985).

Ohlin et al., "Spectrum of Activity of Soluble Intercellular Adhesion Molecule–1 Against Rhinovirus Reference Strains and Field Isolates", Antimicrob. Agents and Chemother. 38:1413–1415 (1994).

Parham, P., "Monoclonal Antibodies Against HLA Products and Their use in Immunaffinity Purification," Methods in Enzymology 92:110–138 (1983).

Pepinsky et al., "The Increased Potency of Crossed–linked Lymphocyte Function–associated Antigen–3 (LFA–3) Multimers Is a Direct Consequence of Changes in Valency", J. Biol. Chem. 266(27):18244–18249 (1991).

Peterson, A. and Seed, B., "Genetic Analysis of Monoclonal Antibody and HIV Binding Sites on the Human Lymophocyte Antigen CD4", Cell 54:65–72 (1988).

Rossman et al., "Structure of a Human Common Cold Virus and Functional Relationship to other Picornaviruses", Nature 317: 145–153 (1985).

Rothlein et al., "A Form of Circulating ICAM–1 In Human Serum", J. Immunol. 147(11):3788–3793 (1991).

Rothlein et al., "A Human Intercellular Adhesion Molecule (ICAM–1) Distinct From LFA–1", J. Immuno. 137(4):1270–1274 (1986).

Ruddle et al., "DNA–Mediated Gene Transfer in Mammalian Gene Cloning", Genetic Engineering 6:319–338 (1984).

Ruoslahti et al., "Synthetic Peptides in the Analysis of Cell Adhesion," in *Synthetic Peptides in Biology and Medicine* Elsevier Science Publishers, pp. 191–197 (1985).

Saiki et al., "Enzymatic Amplification of β–Globin Genomic Sequences and Restriction Site Analysis for Diagnosis of Sicle Cell Anemia," Science 230:1350–1354 (1985).

Sambrook et al., *Molecular Cloning: A Laboratory Manual*, 2d ed. (Cold Spring Harbor Laboratory Press, Cold Spring Harbor, NY, 1989) pp. 1.21–1.52.

Schipper et al., "The Nasal Mucocilliary Clearance: Relevance to Nasal Drug Delivery", Pharm. Res. 8:807–814 (1991).

Scopes, R.K., "Separation By Precipitation," in *Protein Purification: Principles & Practice* (1982) Springler Verlag, NY, pp. 39–46.

Seed, B. and Aruffo, A., "Molecular Cloning of the CD2 antigen, the T–Cell Erythrocyte Receptor, by a Rapid Immunoselection Procedure," PNAS 84:3365–3369 (1987).

Seed, B., "An LFA–3 cDNA Encodes a Phospholipid–Linked Membrane Protein Homologous to its Receptor CD2," Nature 329: 840–842 (1987).

Seth et al., "Circulating ICAM–1 isoforms: Diagnostic Prospects for Inflammatory and Immune Disorders," Lancet 338:83–84 (1991).

Sherman–Gold, R., "Companies Pursue Therapies Based on Complex Cell Adhesion Molecules", Genetic Engineering News pp. 6–7,14 (Jul. 1993).

Sherry, B. and Rueckert, R., "Evidence for at Least Two Dominant Neutralization Antigens on Human Rhinovirus 14," J. Virol. 53(1):137–143 (1985).

Shih, C. and Weinberg, R. A., "Isolation of a Transforming Sequence from a Human Bladder Carcinoma Cell Line," Cell 29: 161–169 (1982).

Shipkowitz et al., "Antiviral Activity of a bis–Benzimidazole Against Experimental Rhinovirus Infections in Chimpanzees", App. Microbiol. 23(1):117–122 (1972).

Siddique et al., "The Poliovirus Sensitivity (PVS) Gene Is on Chromosome 19q12->q13.2", Genomics 3:156–160 (1988).

Simmons et al., "ICAM, an Adhesion Ligand of LFA–1, is Homologous to the Neural Cell Adhesion Molecule NCAM," Nature 331:624–627 (1988).

Simons et al., "Formation of Protein Micelles from Amphiphilic Membrane Proteins", PNAS 75(11):5306–5310 (1978).

Skerra, A. and Pluckthun, A., "Assembly of a Functional Immunoglobulin FV Fragment in Escherichia coli" Science, 240: 1038–1041 (1988).

Smith, T.J., et. al., "The Site of Attachment in Human Rhinovirus 14 for 4 Antiviral Agents that Inhibit Uncoating", Science 233:1286–1293 (1986).

Smith et al., "Blocking of HIV–1 Infectivity by a Soluble, Secreted Form of the CD4 Antigen," Science 238:1704–1707 (1987).

Smith et al., "Modification and Secretion of Human Interleukin 2 Produced in Insect Cells by a Baculovirus Expression Vector", PNAS 82:8404–8408 (1985).

Springer, T.A., "Adhesion Receptors of the Immune System", Nature 346:425–434 (1990).

Staunton et al., "Primary Structure of ICAM–1 Demonstrates Interaction between Members of the Immunoglobulin and Integrin Supergene Families," Cell 52:925–933 (1988).

Staunton et al., "The Arrangement of the Immunoglobulin––Like Domains of ICAM–1 and the Binding Sites for LFA–1 and Rhinovirus," Cell 61:243–254 (1990).

Staunton et al., "A Cell Adhesion Molecule, ICAM–1, is the Major Surface Receptor for Rhinoviruses," Cell 56:849–853 (1989).

Steis et al., "Serum Soluble IL–2 Receptor as a Tumor Marker in Patients with Hairy Cell Leukemia", Blood 71(5):1304–1309 (May 1988).

Sundquist et al., "Influenza Virus ISCOMs: Antibody Response in Animals", Vaccine 6:49–53 (1988).

Sundquist et al., "Influenza Virus ISCOMs: Biochemical Characterization", Vaccine 6:44–48 (1988).

Tomassini, J.E., "Isolation, Characterization and Cloning of the Cellular Receptor for the Major Group of Human Rhinoviruses," Ph.D. Thesis, University of Pennsylvania (1986).

Tomassini, J.E. and Colonno, R. J., "Isolation of a Receptor Protein Involved in Attachment of Human Rhinoviruses," J. Virol. 58(2):290–295 (1986).

Tomassini et al., "cDNA Cloning Reveals that the Major Group Rhinovirus Receptor on HeLa Cells is Intercellular Adhesion Molecule 1," PNAS 86:4907–4911 (1989).

Towbin et. al., "Electrophoretic Transfer of Proteins from Polyacrylamide Gels to Nitrocellulose Sheets: Procedure and Some Applications", PNAS 76(9):4350–4354 (1979).

Traunecker et al., "Highly Efficient Neutralization of HIV with Recombinant CD4–Immunoglobulin Molecules," Nature 339: 68–70 (1989).

Traunecker et al., "Soluble CD4 Molecules Neutralize Human Immunodeficiency Virus Type 1" Nature 331:84–86 (1988).

Turner et al., "Efficacy of Oral WIN 54954 for Prophylaxis of Experimental Rhinovirus Infection", 37:297–300 (1993).

Urlaub, G. and Chasin, L. A., "Isolation of Chinese Hamster Cell Mutants Deficient in Dihydrofolate Reductase Activity," PNAS USA 77(7):4216–4220 (1980).

Wade, N., "Hybridomas: A Potent New Biotechnology," Science 208:692–693 (1980).

Welsh, K.I., "Antibody Production Made Easier," Nature 266: 495 (1977).

Wigler et al., "Transformation of Mammalian Cells with Genes from Procaryotes and Eucaryotes," Cell 16:777–785 (1979).

Williams, A. F., "A Year in the Life of the Immunoglobulin Superfamily", Immunology Today 8(10):298–303 (1987).

Williams, A. F. and Barclay, A. N.,"The Immunoglobulin Superfamily–Domains for Cell Surface Recognition[1,2]", Ann. Rev. Immunol. 6:381–405 (1988).

Winther et al., "Sites of Rhinovirus Recovery After Point Inoculation of the Upper Airway", JAMA 256(13):1763–1767 (1986).

Woods et al., "In Vitro and In Vivo Activities of WIN 54954, a New Broad Spectrum Antipicornavirus Drug", Antimicrob. Agents Chemother 33:2069–2074 (1989).

Zettlmeissl et al., "Expression and Characterization of Human CD4: Immunoglobulin Fusion Proteins," DNA and Cell Biology 9: 347–353 (1990).

Abraham, G. and R.J. Colonno, "Characterization of human rhinoviruses displaced by an anti–receptor monoclonal antibody", J. Virol.62(7):2300–2306 (Jul. 1988).

Ashkenazi, A., L.G. Presta, S.A. Marsters, T.R. Camerato, K.A. Rosen, B.M. Fendly, and D.J. Capon, "Mapping the CD4 binding site for human immunodeficiency virus by alanine scanning mutagenesis", Proc. Natl. Acad. Sci. USA 87:7150–7154 (Sep. 1990).

Brodsky, M.H., M. Warton, R.M. Myers, and D.R. Littman, "Analysis of the site in CD4 that binds to the HIV envelope glycoprotein", J. Immunol. 144(8):3078–3086 (Apr. 1990).

Callahan, P.L., S. Mizutani, and R.J. Colonno, "Molecular cloning and complete sequence determination of RNA genome of human rhinovirus type 14", Proc. Natl. Acad. Sci. USA 82(3):732–6 (Feb. 1985).

Colonno, R.J., "Virus receptors: the Achilles' heel of human rhinoviruses", in Innovations in Antiviral Development and the Detection of Virus Infection, T. Block et al., eds., (Plenum Press, NY, 1992), pp. 61–70.

Colonno, R.J., P.L. Callahan, D.M. Leippe, R.R. Rueckert, and J.E. Tomassini, "Inhibition of rhinovirus attachment by neutralizing monoclonal antibodies and their Fab fragments," J. Virol. 63(1):36–42 (Jan. 1989).

Colonno, R.J., "Cell surface receptors for picornaviruses", Bioassays 5(6):270–4 (1986).

Colonno, R.J., "Molecular interactions between human rhinoviruses and their cellular receptors", Seminars in Virol. 3(2):101–107 (1992).

Colonno, R.J., R.L. LaFemina, C.M. DeWitt, and J.E. Tomassini, "The major–group rhinoviruses utilize the intercellular adhesion molecule 1 ligand as a cellular receptor during infection", in *New Aspects of Positive–Strand RNA Viruses*, Second International Symposium, Vienna, Austria, Meeting Date 1989, Brinton et al., eds. (Am. Soc. Microbiol., Washington, DC, 1990), pp. 257–261.

Colonno, R.J., G. Abraham, and J.E. Tomassini, "Molecular and biochemical aspects of human rhinovirus attachment to cellular receptors", in *Molecular Aspects of Picornavirus Infection and Detection*, [Presentations ICN–UCI Int. Conf. Virol.], Meeting Date 1988, Semler et al., eds. (Am. Soc. Microbiol., Washington, DC, 1989), pp. 169–178.

Colonno, R.J., J.E. Tomassini, P.L. Callahan, and W.J. Long, "Characterization of the cellular receptor specific for attachment of most human rhinovirus serotypes", in *Virus Attachment Entry Cells*, Proc. ASM Conf., Meeting Date 1985, Crowell et al., eds. (Am. Soc. Microbiol. Washington, DC, 1986), pp. 109–115.

Colonno, R.J., "Molecular interactions between human rhinoviruses and the adhesion receptor ICAM–1", in *Microb. Adhes. Invasion*, [Proc. Symp.], meeting date 1990, Hook et al., eds. (Springer, NY, 1992), pp. 33–41.

Colonno, R.J., J.H. Condra, and S. Mizutani, "Interaction of cellular receptors with the canyon structure of human rhinoviruses", in UCLA Symposia on Molecular and Cellular Biology New Series, vol. 90, Cell Biology of Virus Entry, Replication, and Pathogenesis, Taos, NM, Feb. 28–Mar. 5, 1988, Compans et al., eds. (Alan R. Liss, Inc., NY, 1988) pp. 75–84.

Colonno, R.J., R.B. Register, D.W. Lineberger, and C.R. Uncapher, "Identification of ICAM–1 residues critical for attachment of human rhinoviruses", Meeting on Molecular Biology of Human Pathogenic Viruses held at the 20$^{th}$ Annual Meeting of the Keystone Symposia on Molecular and Cellular Biology, Lake Tahoe, CA, Mar. 8–15, 1991, J. Cell Biochem. Suppl. 15(Part E):82, #M310 (1991).

Colonno, R.J., J.H. Condra, S. Mizutani, G. Abraham, P.L. Callahan, J.E. Tomassini, and M.A. Murcko, "Evidence for direct involvement of the rhinovirus canyon with cellular receptors", in Symposium on Cell Biology of Virus Entry, Replication and Pathogenesis, Positive Strand RNA Viruses, 17$^{th}$ Annual UCLA meeting on Molecular and Cellular Biology, Taos, NM, Feb. 28–Mar. 5, 1988, J. Cell. Biochem. Suppl., 0 (12 Part C):4, #J005 (1988).

Colonno, R.J., J.E. Tomassini, and P.L. Callahan, "Isolation and characterization of a monoclonal antibody which blocks attachment of human rhinoviruses", in UCLA Symposia on Molecular and Cellular Biology , New Series, vol. 54, Positive Strand RNA Viruses, Keystone, CO Apr. 20–26, 1986, Brinton et al., eds. (Alan R. Liss, Inc., NY, 1987), pp. 93–102.

Colonno, R.J., J.E. Tomassini, and P.L. Callahn, "Huan rhinovirus attachment requires a specific cellular receptor protein", in Symposium on Positive Strand RNA Viruses, 15$^{th}$ Annual Meeting of the UCLA Symposia on Molecular and Cellular Biology, Apr. 20–26, 1986, J. Cell. Biochem Suppl., 0 (10 Part D):266, #Q4 (1986).

Condra, J.H., V.V. Sardan, J.E. Tomassini, A.J. Schlabach, M.–E. Davies, D.W. Lineberger, D.J. Graham, and R.J. Colonno,, "Bacterial expression of antibody fragments that block human rhinovirus infection of cultured cells", J. Biol. Chem. 265(4):2292–2295 (Feb. 1990).

Cordingley, M.G., P.L. Callahan, V.V. Sardana, V.M. Garsky, and R.J. Colonno, "Substrate requirements of human rhinovirus 3C protease for peptide cleavage in vitro", J. Biol. Chem. 265(16):9062–5 (1990).

Cordingley, M.G., R.B. Register, P.l. Callahan, V.M. Garsky, and R.J. Colonno, "Cleavage of small peptides in vitro by human rhinovirus 14 3C protease expressed in Escherichia coli", J. Virol. 63(12):5037–45 (Dec. 1989).

Dewalt, P.G., M.A. Lawson, R.J. Colonno, and B.L. Semler, "Chimeric picornavirus polyproteins demonstrate a common 3C proteinase substrate specificity", J. Virol. 63(8):3444–3452 (1989).

Dick, E.C., and C.R. Dick, "Natural and Experimental Infections of Nonhuman Primates with Respiratory Viruses", Laboratory Animal Science 24(1): 177–181 (1974).

Emini, E.A., W.A. Schleif, R.J. Colonno, and E. Wimmer, "Antigenic conservation and divergence between the viral–specific proteins of poliovirus type 1 and various picornaviruses", Virol. 140(1):13–20 (1985).

Hazuda, D., V. Sardana, P. Callahan, M. Cordingley, and R. Colonno, "Chemical approaches to mapping the active site thiol of human rhinovirus 3C protease", Joint Meeting of the American Society for Biochemistry and Molecular Biology and the American Association of Immunologists, New Orleans, LA, Jun. 4–7, 1990, Fed. Am. Soc. Exp. Biol. J. 4(7):#1605 (1990).

Johnston, S.C., M.L. Dustin, M.L. Hibbs, and T.A. Springer, "On the species specificity of the interaction of LFA–1 with intercellular adhesion molecules", J. Immunol. 145(4):1181–1187 (Aug. 1990).

Lamarre, D., D.J. Capon, D.R. Karp, T.Gregory, E.O. Long, and R.–P. Sekaly, "Class II MHC molecules and the HIV envelope glycoprotein interact with functionally distinct regions of the molecule", EMBO J. 8(11):3271–3277 (1989).

Lineberger, D.W., C.R. Uncapher, D.J. Graham, and R.J. Colonno, "Domains 1 and 2 of ICAM–1 are sufficient to bind human rhinoviruses", Virus Research 24(2): 173–86 (1992).

Maddon, P.J., A.G. Dalgleish, J.S. McDougal, P.R. Clapham, R.A. Weiss, and R. Axel, "The T4 Gene Encodes the AIDS Virus Receptor and is Expressed in the Immune System and the Brain", Cell 47: 333–348 (Nov. 1986).

Mendelsohn, C.L., E. Wimmer, and V.R. Racaniello, "Cellular receptor for poliovirus: molecular cloning, nucleotide sequence, and expression of a new member of the immunoglobulin superfamily", Cell 56:855–865 (Mar. 1989).

Mizutani, S., and R.J. Colonno, In vitro synthesis of an infectious RNA from cDNA clones of human rhinovirus type 14;, J. Virol. 56(2):628–32 (Nov. 1985).

Register, R.B., C.R. Uncapher, A.M. Naylor, D.W. Lineberger, and R.J. Colonno, "Human–murine chimeras of ICAM–1 identify amino acid residues critical for rhinovirus and antibody binding", J. Virol. 65(12):6589–6596 (Dec. 1991).

Rueckert, R. B. Sherry, A. Mosser, R. Colonno, and M. Rossman, "Location of four neutralization antigens on the three–dimensional surface of a common–cold picornavirus, human rhinovirus 14", in *Virus Attachment Entry Cells*, Proc. ASM Conf., Meeting date 1985, Crowell et al., eds. (Am. Soc. Microbiol., Washington, DC, 1986), pp. 21–27.

Sherry, B., A. G. Mosser, R.J. Colonno, and R.R. Rueckert, "Use of monoclonal antibodies to identify four neutralizing immunogens on a common cold picornavirus, human rhinovirus 14", J. Virol. 57(1):246–57 (Jan. 1986).

Tomassini, J.E., T.R. Maxson, and R.J. Colonno, "Biochemical characterization of a glycoprotein required for rhinovirus attachment", J. Biol. Chem. 264(3):1656–1662 (Jan. 1989).

Tomassini, J.E., and R.J. Colonno, "Isolation and characterization of a cellular receptor involved in attachment of human rhinoviruses to cells", in Symposium on Positive Strand RNA Viruses, 15th Annual Meeting of the UCLA Symposia on Molecular and Cellular Biology, Apr. 20–26, 1986, J. Cell. Biochem. Suppl., 0 (10 Part D):300, #Q92 (1986).

Braude, A. (ed.s), "Infectious Diseases and Medical Microbiology, 2nd edition, W.B. Saunders Co., Philadelphia, PA, (1986) chapter 65 Picornaviruses", pp. 521–529.

Gennaro, A.R. (ed.), Remington's Pharmaceutical Sciences, 18th edition, Mack Publishing Co., Easton, PA (1990), "Drug Absorption, Action and Disposition", pp. 707–721.

Martin et al., "Efficient Neutralization and Disruption of Rhinovirus by Chimeric ICAM–1/Immunoglobulin Molecules", J. Virology, 67(6):3561–3568 (Jun. 1993).

Hendley et al., "Transmission of Rhinovirus Colds By Self–Inoculation", The New England Journal of Medicine, 288(26):1361–1364 (Jun. 28, 1973).

Hendley, J. O., and Gwaltney, J. M., Jr., "Mechanisms of Transmission of Rhinovirus Infections", Epidemiologic Reviews, 10:242–257 (1988).

Suter, David, Associated Press, "Tests for a Nasal Spray to Deflect Cold Viruses", New York Times, Sep. 20, 1995.

Manning, Anita, "War on Bacteria Mix of Victories Amid Warnings", USA Today, Sep. 20, 1995.

Haney, Daniel Q., "Beyond Chicken Soup. Nasal Spray Keeps Chimps From Catching Cold Virus", St. Louis Post Dispatch, Sep. 20, 1995.

Associated Press, "Common Colds: Nasal Spray May Help Keep The Sniffles Away", Atlanta Constitution, Sep. 20, 1995.

Associated Press, "Drug Sprays Away Colds", New York Post, Sep. 20, 1995.

Haney, Daniel Q., Associated Press, "The Cold War: Scientists Develop Spray That May End Sniffles", Arizona Republic, Sep. 20, 1995.

Haney, Daniel Q., Associated Press, "For Colds, Nasal Spray Holds Hope. A Protein Swamps The Virus With Potential Targets In The Nose. Its a Decoy Trick", Philadelphia Inquirer, Sep. 20, 1995.

Associated Press, "Simple Nasal Spray May Be Able To Keep Common Cold Away. Medicine Successful On Chimps So Far", Washington Times, Sep. 20, 1995.

Associated Press, "Doctors Sniffing Out Spray to Fight Colds", Denver Post, Sep. 20, 1995.

Associated Press, "Someday Soon, A Simple Sniff Should Snuff The Sniffles", Houston Chronicle, Sep. 20, 1995.

Haney, Daniel Q., Associated Press, "Spray May Ward Off Sniffles. Nasal Treatment Studied To Keep Cold Viruses From Invading Victim", Denver—Rocky Mountain News, Sep. 20, 1995.

Haney, Daniel Q., Associated Press, "Scientists Make Headway In Cold War With Nose Spray", Chicago Sun–Times, Sep. 20, 1995.

Haney, Daniel Q., Associated Press, "Labs Busy Working On Nose Spray To Keep Colds Away", Charlotte Observer, Sep. 20, 1995.

Associated Press, "Nasal Spray May Prevent Sniffles", Miami Herald, Sep. 20, 1995.

Associated Press, "Cure For The Cold? No, But Prevention May Be Spray Away", San Diego Union–Tribune, Sep. 20, 1995.

Haney, Daniel Q., "Nasal Spray Touted As Next–Best Thing To Cure For Colds", The Montreal Gazette, Sep. 20, 1995.

Associated Press, "Scientists Feel They Can Develop Spray To Keep The Sniffles Away", The Spectator, Sep. 20, 1995.

Haney, Daniel Q., Associated Press, "New Nasal Spray May Take Sniffles Out Of Common Cold", Cleveland Plain Dealer, Sep. 20, 1995.

Associated Press, No Cure, But Nothing To Sniff(le) At. Nasal Spray To Block Common Cold Is In The Works, Minneapolis Star Tribune, Sep. 20, 1995.

Haney, Daniel Q., Associated Press, "Out Front: Progress On Cold Front. Spray May Ward Off Sniffles. Medicine Is First To Block Infection", Sep. 19, 1995.

Monitoring Report, "Cure For Colds Sep. 18 to Sep. 20", Video Monitoring Services of America, a Burrelle's Affiliate, New York, New York, pp. 1–3, Sep. 20, 1995.

Al–Nakib, W., P.G. Higgins, G.I. Barrow, D.A.J. Tyrrell, K. Andries, G. Vanden Bussche, N. Taylor, and P.A.J. Janssen, "Suppression of Colds in Human Volunteers Challenged with Rhinoviurs by a New Synthetic Drug (R61837)", Antimicrobial Agents and Chemotherapy 33(4): 522–525 (Apr. 1989).

Amzel, L. M., and R.J. Poljak, "Three–Dimensional Structure of Immunoglobulins", Ann. Rev. Biochem. 48: 961–997 (1979).

Becker, J. W., and G.N.Reeke, Jr., "Three–dimensional structure of $\beta_2$–microglobulin", Proc. Natl. Acad. Sci. USA 82: 4225–4229 (Jun. 1985).

Becker, J. W., H.P. Erickson, S. Hoffman, B.A. Cunningham, and G.M. Edelman, "Topology of cell adhesion molecules", Proc. Natl. Acad. Sci. USA, 86: 1088–1092 (Feb. 1989).

Bjorkman, P. J., M.A. Saper, B. Samraoui, W.S. Bennett, J.L. Strominger, and D.C. Wiley, "Structure of the human class I histocompatibility antigen, HLA–A2", Nature 329: 506–512 (Oct. 1987).

Colman, P.M., "Structure of Antibody–Antigen Complexes: Implications for Immune Recognition", Advances in Immunology 43: 99–132 (1988).

Colonno, R. J., J.H. Condra, S. Mizutani, P.L. Callahan, M.–E.Davies, and M.A. Murcko, "Evidence for the direct involvement of the rhinovirus canyon in receptor binding", Proc. Natl. Acad. Sci. USA 85: 5449–5453 (Aug. 1988).

Craig, A. G. and A.R. Berendt, "The Role of ICAM–1 as a Receptor for Rhinovirus and Malaria", in *Integrins and ICAM–1 in Immune Responses*, N. Hodd, ed. (Chem Immunol. Basel, Karger, 1991), vol. 50, pp. 116–134 (1991).

Crump, C. E., Arruda, and F.G. Hayden, "Comparative Antirhinoviral Activities of Soluble Intercellular Adhesion Molecule–1 (sICAM–1) and Chimeric ICAM–1/Immunoglobulin A Molecule", Antimicrobial Agents and Chemotherapy 38(6): 1425–1427 (Jun. 1994).

Dayhoff, M. O., W.C. Barker, and L. T. Hunt, "Establishing Homologies in Protein Sequences", Methods in Enzymology 91: 524–545 (1983).

Dearden, C., W. Al–Nakib, K. Andries, R. Woestenborghs, and D.A.J. Tyrrell, "Drug resistant rhinoviruses from the nose of experimentally treated volunteers", Arch. Virol. 109: 71–81 (1989).

Dustin, M. L. and T.A. Springer, "Lymphocyte Function––associated Antigen–1 (LFA–1) Interaction with Intercellular Adhesion Molecule–1 (ICAM–1) is One of At Least Three Mechanisms for Lymphocyte Adhesion to Cultured Endothelial Cells," J. Cell Biol. 107: 321–331 (Jul. 1988).

Ezekovitz, R.A.B., R.B. Sim, G.G. MacPherson, and S. Gordon, "Interaction of Human Monocytes, Macrophages, and Polymorphonuclear Leukocytes with Zymosan in Vitro: Role of Type 3 Compliment Receptors and Macrophage Derived Complement", J. Clin. Invest. 76: 2368–2376 (Dec. 1985).

Greve, J. M., C.P. Forte, C.W. Marlor, A.M. Meyer, H. Hoover–Litty, D. Wunderlich, and A. McClelland "Mechanisms of Receptor–Mediated Rhinovirus Neutralization Defined by Two Soluble Forms of ICAM–1", J. Virol. 65(11): 6015–6023 (Nov. 1991).

Guttman, N., and D. Baltimore, "Plasma Membrane Component Able to Bind and Alter Virions of Poliovirus Type 1: Sutides on Cell–Free Alteration Using a Simplified Assay", Virol. 82: 25–36 (1977).

Gwaltney, J. M., Jr., and J.O. Hendley, "Rhinovirus Transmission: One if by Air, Two if by Hand", Trans. Am. Clin. Climatol. Assoc. 89: 194–200 (1977).

Gwaltney, J. M.,Jr., and J.O. Hendley, "Rhinovirus Transmission One if by Air, Two if by Hand", Am. J. Epid. 107(5): 357–361 (May 1978).

Gwaltney, J. M., Jr., "Rhinovirus colds: epdimiology, clinical characteristics and transmission", Eur. J. Respir. Dis. 64 (suppl. 128): 336–339 (1983).

Gwaltney, J. M., Jr., "Rhinoviruses", Yale J. Biol. Med. 48: 17–45 (1975).

Hayden, F. G., and J.M. Gwaltney, Jr., "Intranasal Interferon–$\alpha_2$ Treatment of Experimental Rhinoviral Colds", J. Infect. Dis. 150(2): 174–180 (Aug. 1984).

Hendley, J.O., and J.M. Gwaltney, Jr., "Mechanisms of Transmission of Rhinovirus Infections", Epidemiologic Reviews 10: 242–258 (1988).

Horley, K. J., C. Carpenito, B. Baker, and F. Takei, "Molecular cloning of murine intercellular adhesion molecule (ICAM–1)", EMBO J. 8(10): 2889–2896 (1989).

Jacobs, K., C. Shoemaker, R. Rudersdorf, S.D. Neill, R.J. Kaufman, A. Mufson, J. Seehra, S.S. Jones, R. Hewick, E.F. Fritsch, M. Kawakita, T. Shimizu, and T. Miyake, "Isolation and characterization of genomic and cDNA clones of human erythropoietin", Nature 313: 806–810 (Feb. 1985).

Kim S., T.J. Smith, M.S. Chapman, M.G. Rossmann, D.C. Pevear, F.J. Dutko, P.J. Felock, G.D. Diana, and M.A. McKinlay, "Crystal Structure of Human Rhinovirus Serotype 1A (HRV1A)", J. Med. Biol. 210: 91–111 (1989).

Layne S. P., M.J. Merges, M. Dembo, J.L. Spouge, and P.L. Nara, "HIV requires multiple gp120 molecules for CD4–mediated infection", Nature 346: 277–279 (Jul. 1990).

Leonard, W. J., J.M. Depper, G.R. Crabtree, S. Rudikoff, J. Pumphrey, R.J. Robb, M. Krönke, P.B. Svetlik, N.J. Peffer, T.A. Waldmann, and W.C. Greene, "Molecular cloning and expression of cDNAs for the human interleukin–2 receptor", Nature 311: 626–631 (Oct. 1984).

Leszczynski, J. F., and G.D. Rose, "Loops in Globular Proteins: A Novel Category of Secondary Structure", Science 234: 849–855 (Nov. 1986).

Lineberger, D. W., D.J. Graham, J.E. Tomassini, and R.J. Colonno, "Antibodies that Block Rhinovirus Attachment Map to Domain 1 of the Major Group Receptor", J. Virol. 64(6): 2582–2587 (Jun. 1990).

Martin, S., J.M. Casanovas, D.E. Staunton, and T.A. Springer, "Erfolgreiche Blockade von Rhinovirusinfektionen durch ICAM–1–Immunoglobulinchimare in vitro", Med. Klin. 88(4): 193–197 (1993).

McPherson, J. M., and D.J. Livingston, "Protein Engineering: New Approaches to Improved Therapeutic Proteins, Part I", in Biotech. Trends, S. Petska, ed. (Pharmaceutical Technology, May 1989).

Livingston, D. J., and J.M. McPherson, "Protein Engineering: New Approaches to Improved Therapeutic Proteins, Part II", in Biotech. Trends, S. Petska, ed. (Pharmaceutical Technology, Jun. 1989).

McPherson, J. M., and D.J. Livingston, "Protein Engineering: New Approaches to Improved Therapeutic Proteins, Part III", in Biotech. Trends, S. Petska, ed. (Pharmaceutical Technology, Sep. 1989).

McClelland, A., M.E.Kamarck, and F.H. Ruddle, "Molecular Cloning of Receptor Genes by Transfection", Methods in Enzymology 147: 280–291 (1987).

Minor, P. D., "Chapter 2: Growth, Assay and Purification of Picornaviruses", in Virology: a practical approach (IRL Press, Washington, D.C., 1985), pp. 25–41.

Minor, P. D., P.A. Pipkin, D. Hockley, G.C. Schild, and J.W. Almond, "Monoclonal antibodies which block cellular receptors of poliovirus", Virus Res. 1: 203–212 (1984).

Morein B., "Potentiation of the Immune Response by Immunization with Antigens in Defined Multimeric Physical Forms", Vet. Immunol. Immunopathol. 17: 153–159 (1987).

Ockenhouse, C.F., R. Betageri, T.A. Springer, and D.E. Staunton, "Plasmodium falciparum–Infected Erythrocytes Bind ICAM–1 at a Site Distinct from LFA–1, Mac–1, and Human Rhinovirus", Cell 68: 63–69 (Jan. 1992).

Peppel, K., D. Crawford, and B. Beutler, "A Tumor Necrosis Factor (TNF) Receptor–IgG Heavy Chain Chimeric Protein as a Bivalent Antagonist of TNF Activity", J. Exp. Med. 174: 1483–1489 (Dec. 1991).

Pevear, D. C., M.J. Fancher, P.J. Felock, M.g. Rossmann, M.S. Miller, G. Diana, A.M. Treasurywala, M.A. McKinlay, and F.J. Dutko, "Conformational Change in the floor of the Human Rhinovirus Canyon Blocks Adsorption to HeLa Cell Receptors", J. Virol. 63(5): 2002–2007 (May 1989).

Plow, E. F., M.D. Pierschbacher, E. Ruoslahti, G.A. Marguerie, and M.H. Ginsberg, "The effect of Arg–Gly–Asp–containing peptides on fibrinogen and von Willebrand factor binding to platelets", Proc. Natl. Acad. Sci. USA 82: 8057–8061 (1985).

Ray, C. G., "Chapter 32: Respiratory Viruses", in Medical Microbiology, an Introduction to Infectious Diseases, 2nd Ed, J. C. Sherris, ed. (Elsevier, New York, 1990), pp. 499–516.

Roesing, T. G., P.A. Toselli, and R.L. Crowell, "Elution and Uncoating of Coxsackievirus B3 by Isolated HeLa Cell Plasma Membranes", J. Virol. 15(3): 654–667 (Mar. 1975).

Rossmann, M. G., "The Canyon Hypothesis. Hiding the Host Cell Receptor Attachment Site on a Viral Surface from Immune Surveillance", J. Biol. Chem. 264(25): 14587–14590 (Sep. 1989).

Saiki, R.K., D.H. Gelfand, S. Stoffel, S.J. Scharf, R. Higuchi, G.T. Horn, K.B. Mullis, and H.A. Erlich, "Primer–Directed Enzymatic Amplification of DNA with a Thermostable DNA Polymerase", Science 239: 487–491 (Jan. 1988).

Sayre, P.H., R.E. Hussey, H.–C. Chang, T.L. Ciardelli, and E.L. Reinherz, "Structural and Binding Analysis of a Two Domain Extracellular CD2 Molecule", J. Exp. Med. 169: 995–1009 (Mar. 1989).

Siu, G., S.M. Hedrick, and A.A. Brian, "Isolation of the Murine Intercellular Adhesion Molecule 1 (ICAM–1) Gene", J. Immun. 143(11): 3813–3820 (Dec. 1989).

Skern, T., W. Sommergruber, D. Blass, P. Gruendler, F. Fraundorfer, C. Pieler, I. Fogy, and E. Kuechler, "Human rhinovirus 2: complete nucleotide sequence and proteolytic processing signals in the capsid protein region", Nucleic Acids Research 13(6): 2111–2126 (1985).

Smilek, D.E., D.C. Wraith, S. Hodgkinson, S. Swivedy, L. Steinman, and H.O. McDevitt, "A single amino acid change in a mylelin basic protein peptide confers the capacity to prevent rather than induce experimental autoimmune encephalomyelitis", Proc. Natl. Acad. Sci. USA 88: 9633–9637 (Nov. 1991).

Staunton, D.E., M.L. Dustin, and T.A. Springer, "Functional cloning of ICAM–2, a cell adhesion ligand for LFA–1 homologous to ICAM–1", Nature 339: 61–64 (May 1989).

Staunton, D.E., C.F. Ockenhouse, and T.A. Springer, "Soluble Intercellular Adhesion Molecule 1–Immunoglobulin G1 Immunoadhesin Mediates Phagocytosis of Malaria–infected Erythrocytes", J. Exp. Med. 176: 1471–1476 (Nov. 1992).

Uncapher, C. R., C.M. DeWitt, and R.J. Colonno, "The Major and Minor Group Receptor Families Contain All but One Human Rhinovirus Serotype", Virology 180: 814–817 (1991).

Wickner W. T., and H.F. Lodish, "Multiple Mechanisms of Protein Insertion Into and Across Membranes", Science 230: 400–407 (Oct. 1985).

Weis, W., J.H. Brown, S. Cusack, J.C. Paulson, J.J. Skehel, and D.C. Wiley, "Structure of the influenza virus haemagglutinin complexed with its receptor, sialic acid", Nature 333: 426–431 (Jun. 1988).

R&D Systems (Minneapolis, MN), 1994 Catalog, Item # BBE 1B, "Human Soluble ICAM–1".

"Chapter 9, Introduction of DNA into Mammalian Cells", Current Protocols in Molecular Biology 1997: 9.0.1–9.9.16 (1997).

British Biotechnology, Ltd. (Oxford, England), 1993 Product Catalog, Item # BBE 1, "Soluble ICAM–1 Elisa".

Marsh, J. W., et al., in Immunotoxins, A. E. Frankel (ed), Kluwer Academic Publishers, Boston (1988), "Antibody–toxin conjugation".

Marlin, S. D., et al., Cell 51:813–819 (Dec. 4, 1987), "Purified Intercellular adhesion molecule–1 (ICAM–1) is a ligand for lymphocyte function–associated antigen 1 (LFA–1)".

Staunton, D. E., et al., Cell 61:243–254 (Apr. 20, 1990), "The arrangement of the immunoglobulin–like domains of ICAM–1 and the binding sites for LFA–1 and rhinovirus".

Tomassini, J. E., et al., J. Virology 58(2):290–295 (May, 1986), "Isolation of a receptor protein involved in attachment of human rhinoviruses".

Towbin, H., et al., PNAS 76:4350–4354 (1979), "Electrophoretic transfer of protiens from polyacrylamide gels to nitrocellulose sheets: procedure and some applications".

Marsh, J.W. et al., in *Immunotoxins* (Frankel, ed) Kluwer Academic Publishers (1988). pp. 213–237.

Marlin, S. D. et al., Cell 51:813–819 (1987) "Purified Intercellular Adhesion Molecule–1 (ICAM–1) . . . ".

Tomassini, J.E. et al., J. Virol. 58(2):290–295 (1986) "Isolation of a receptor protein involved in attachment of human rhinoviruses".

SEQUENCE LISTING (1) GENERAL INFORMATION:

(iii) NUMBER OF SEQUENCES: 11

(2) INFORMATION FOR SEQ ID NO:1:

(i) SEQUENCE CHARACTERISTICS:
      (A) LENGTH: 505
      (B) TYPE: amino acids
      (D) TOPOLOGY: linear (ii) MOLECULE TYPE: protein (iii) HYPOTHETICAL: no (ix) FEATURE:
      (A) NAME/KEY: ICAM-1 protein (x) PUBLICATION INFORMATION:
      (A) AUTHORS: Staunton, D.E., Marlin, S.D., Stratowa, C.,
         Dustin, M.L., and Springer, T.A.
      (B) TITLE: Primary Structure of ICAM-1 Demonstrates
         Interaction between Members of the Immunoglobulin and
         Integrin Supergene Families
      (C) JOURNAL: Cell
      (D) VOLUME: 52
      (F) PAGES: 925-933
      (G) DATE: March 25, 1988

(xi) SEQUENCE DESCRIPTION: SEQ ID NO:1:

Gln Thr Ser Val Ser Pro Ser Lys Val Ile Leu Pro Arg Gly Gly
             5                  10               15

Ser Val Leu Val Thr Cys Ser Thr Ser Cys Asp Gln Pro Lys Leu
            20                25              30

```
Leu Gly Ile Glu Thr Pro Leu Pro Lys Lys Glu Leu Leu Pro
                35              40                  45

Gly Asn Asn Arg Lys Val Tyr Glu Leu Ser Asn Val Gln Glu Asp
                50              55                  60

Ser Gln Pro Met Cys Tyr Ser Asn Cys Pro Asp Gly Gln Ser Thr
                65              70                  75

Ala Lys Thr Phe Leu Thr Val Tyr Trp Thr Pro Glu Arg Val Glu
                80              85                  90

Leu Ala Pro Leu Pro Ser Trp Gln Pro Val Gly Lys Asn Leu Thr
                95              100                 105

Leu Arg Cys Gln Val Glu Gly Gly Ala Pro Arg Ala Asn Leu Thr
                110             115                 120

Val Val Leu Leu Arg Gly Glu Lys Glu Leu Lys Arg Glu Pro Ala
                125             130                 135

Val Gly Glu Pro Ala Glu Val Thr Thr Thr Val Leu Val Arg Arg
                140             145                 150

Asp His His Gly Ala Asn Phe Ser Cys Arg Thr Glu Leu Asp Leu
                155             160                 165

Arg Pro Gln Gly Leu Glu Leu Phe Glu Asn Thr Ser Ala Pro Tyr
                170             175                 180

Gln Leu Gln Thr Phe Val Leu Pro Ala Thr Pro Pro Gln Leu Val
                185             190                 195

Ser Pro Arg Val Leu Glu Val Asp Thr Gln Gly Thr Val Val Cys
                200             205                 210

Ser Leu Asp Gly Leu Phe Pro Val Ser Glu Ala Gln Val His Leu
                215             220                 225

Ala Leu Gly Asp Gln Arg Leu Asn Pro Thr Val Thr Tyr Gly Asn
                230             235                 240

Asp Ser Phe Ser Ala Lys Ala Ser Val Ser Val Thr Ala Glu Asp
                245             250                 255

Glu Gly Thr Gln Arg Leu Thr Cys Ala Val Ile Leu Gly Asn Gln
                260             265                 270

Ser Gln Glu Thr Leu Gln Thr Val Thr Ile Tyr Ser Phe Pro Ala
                275             280                 285

Pro Asn Val Ile Leu Thr Lys Pro Glu Val Ser Glu Gly Thr Glu
                290             295                 300

Val Thr Val Lys Cys Glu Ala His Pro Arg Ala Lys Val Thr Leu
                305             310                 315

Asn Gly Val Pro Ala Gln Pro Leu Gly Pro Arg Ala Gln Leu Leu
                320             325                 330

Leu Lys Ala Thr Pro Glu Asp Asn Gly Arg Ser Phe Ser Cys Ser
                335             340                 345

Ala Thr Leu Glu Val Ala Gly Gln Leu Ile His Lys Asn Gln Thr
                350             355                 360

Arg Glu Leu Arg Val Leu Tyr Gly Pro Arg Leu Asp Glu Arg Asp
                365             370                 375

Cys Pro Gly Asn Trp Thr Trp Pro Glu Asn Ser Gln Gln Thr Pro
                380             385                 390

Met Cys Gln Ala Trp Gly Asn Pro Leu Pro Glu Leu Lys Cys Leu
                395             400                 405

Lys Asp Gly Thr Phe Pro Leu Pro Ile Gly Glu Ser Val Thr Val
                410             415                 420
```

```
Thr Arg Asp Leu Glu Gly Thr Tyr Leu Cys Arg Ala Arg Ser Thr
            425                 430                 435

Gln Gly Glu Val Thr Arg Glu Val Thr Val Asn Val Leu Ser Pro
            440                 445                 450

Arg Tyr Glu Ile Val Ile Ile Thr Val Ala Ala Ala Val Ile
            455                 460                 465

Met Gly Thr Ala Gly Leu Ser Thr Tyr Leu Tyr Asn Arg Gln Arg
            470                 475                 480

Lys Ile Lys Lys Tyr Arg Leu Gln Gln Ala Gln Lys Gly Thr Pro
            485                 490                 495

Met Lys Pro Asn Thr Gln Ala Thr Pro Pro
            500                 505
```

(2) INFORMATION FOR SEQ ID NO:2:

(i) SEQUENCE CHARACTERISTICS:
        (A) LENGTH: 1656
        (B) TYPE: nucleic acid
        (C) STRANDEDNESS: single
        (D) TOPOLOGY: linear (ii) MOLECULE TYPE: other nucleic acid (iii) HYPOTHETICAL: no (iv) ANTI-SENSE: no (ix) FEATURE:
        (A) NAME/KEY: ICAM-1 coding sequence (x) PUBLICATION INFORMATION:
        (A) AUTHORS: Staunton, D.E., Marlin, S.D., Stratowa, C.,
            Dustin, M.L., and Springer, T.A.
        (B) TITLE: Primary Structure of ICAM-1 Demonstrates
            Interaction between Members of the Immunoglobulin and
            Integrin Supergene Families
        (C) JOURNAL: Cell
        (D) VOLUME: 52
        (F) PAGES: 925-933
        (G) DATE: March 25, 1988
        (K) RELEVANT RESIDUES IN SEQ ID NO:2: From 58 to
            1653

(xi) SEQUENCE DESCRIPTION: SEQ ID NO:2:

```
gcgccccagt cgacgctgag ctcctctgct actcagagtt gcaacctcag cctcgctatg      60
gctcccagca gccccccggcc cgcgctgccc gcactcctgg tcctgctggg ggctctgtta    120
ccaggacctg gcaatgcc cag aca tct gtg tcc ccc tca aaa gtc atc ctg       171
             Gln Thr Ser Val Ser Pro Ser Lys Val Ile Leu
              1               5                  10 ccc cgg gga ggc tcc gtg ctg gtg aca tgc agc acc tcc tgt gac cag       219
Pro Arg Gly Gly Ser Val Leu Val Thr Cys Ser Thr Ser Cys Asp Gln
             15                  20                  25 ccc aag ttg ttg ggc ata gag acc ccg ttg cct aaa aag gag ttg ctc       267
Pro Lys Leu Leu Gly Ile Glu Thr Pro Leu Pro Lys Lys Glu Leu Leu
         30                  35                  40 ctg cct ggg aac aac cgg aag gtg tat gaa ctg agc aat gtg caa gaa       315
Leu Pro Gly Asn Asn Arg Lys Val Tyr Glu Leu Ser Asn Val Gln Glu
     45                  50                  55 gat agc caa cca atg tgc tat tca aac tgc cct gat ggg cag tca aca       363
Asp Ser Gln Pro Met Cys Tyr Ser Asn Cys Pro Asp Gly Gln Ser Thr
 60                  65                  70                  75 gct aaa acc ttc ctc acc gtg tac tgg act cca gaa cgg gtg gaa ctg       411
Ala Lys Thr Phe Leu Thr Val Tyr Trp Thr Pro Glu Arg Val Glu Leu
             80                  85                  90
```

```
gca ccc ctc ccc tct tgg cag cca gtg ggc aag aac ctt acc cta cgc      459
Ala Pro Leu Pro Ser Trp Gln Pro Val Gly Lys Asn Leu Thr Leu Arg
             95                 100                 105 tgc cag gtg gag ggt ggg gca ccc cgg gcc aac ctc acc gtg gtg ctg      507
Cys Gln Val Glu Gly Gly Ala Pro Arg Ala Asn Leu Thr Val Val Leu
        110                 115                 120 ctc cgt ggg gag aag gag ctg aaa cgg gag cca gct gtg ggg gag ccc      555
Leu Arg Gly Glu Lys Glu Leu Lys Arg Glu Pro Ala Val Gly Glu Pro
    125                 130                 135 gct gag gtc acg acc acg gtg ctg gtg agg aga gat cac cat gga gcc      603
Ala Glu Val Thr Thr Thr Val Leu Val Arg Arg Asp His His Gly Ala
140                 145                 150                 155 aat ttc tcg tgc cgc act gaa ctg gac ctg cgg ccc caa ggg ctg gag      651
Asn Phe Ser Cys Arg Thr Glu Leu Asp Leu Arg Pro Gln Gly Leu Glu
                160                 165                 170 ctg ttt gag aac acc tcg gcg ccc tac cag ctc cag acc ttt gtc ctg      699
Leu Phe Glu Asn Thr Ser Ala Pro Tyr Gln Leu Gln Thr Phe Val Leu
            175                 180                 185 cca gcg act ccc cca caa ctt gtc agc ccc cgg gtc cta gag gtg gac      747
Pro Ala Thr Pro Pro Gln Leu Val Ser Pro Arg Val Leu Glu Val Asp
        190                 195                 200 acg cag ggg acc gtg gtc tgt tcc ctg gac ggg ctg ttc cca gtc tcg      795
Thr Gln Gly Thr Val Val Cys Ser Leu Asp Gly Leu Phe Pro Val Ser
    205                 210                 215 gag gcc cag gtc cac ctg gca ctg ggg gac cag agg ttg aac ccc aca      843
Glu Ala Gln Val His Leu Ala Leu Gly Asp Gln Arg Leu Asn Pro Thr
220                 225                 230                 235 gtc acc tat ggc aac gac tcc ttc tcg gcc aag gcc tca gtc agt gtg      891
Val Thr Tyr Gly Asn Asp Ser Phe Ser Ala Lys Ala Ser Val Ser Val
                240                 245                 250 acc gca gag gac gag ggc acc cag cgg ctg acg tgt gca gta ata ctg      939
Thr Ala Glu Asp Glu Gly Thr Gln Arg Leu Thr Cys Ala Val Ile Leu
            255                 260                 265 ggg aac cag agc cag gag aca ctg cag aca gtg acc atc tac agc ttt      987
Gly Asn Gln Ser Gln Glu Thr Leu Gln Thr Val Thr Ile Tyr Ser Phe
        270                 275                 280 ccg gcg ccc aac gtg att ctg acg aag cca gag gtc tca gaa ggg acc     1035
Pro Ala Pro Asn Val Ile Leu Thr Lys Pro Glu Val Ser Glu Gly Thr
    285                 290                 295 gag gtg aca gtg aag tgt gag gcc cac cct aga gcc aag gtg acg ctg     1083
Glu Val Thr Val Lys Cys Glu Ala His Pro Arg Ala Lys Val Thr Leu
300                 305                 310                 315 aat ggg gtt cca gcc cag cca ctg ggc ccg agg gcc cag ctc ctg ctg     1131
Asn Gly Val Pro Ala Gln Pro Leu Gly Pro Arg Ala Gln Leu Leu Leu
                320                 325                 330 aag gcc acc cca gag gac aac ggg cgc agc ttc tcc tgc tct gca acc     1179
Lys Ala Thr Pro Glu Asp Asn Gly Arg Ser Phe Ser Cys Ser Ala Thr
            335                 340                 345 ctg gag gtg gcc ggc cag ctt ata cac aag aac cag acc cgg gag ctt     1227
Leu Glu Val Ala Gly Gln Leu Ile His Lys Asn Gln Thr Arg Glu Leu
        350                 355                 360 cgt gtc ctg tat ggc ccc cga ctg gac gag agg gat tgt ccg gga aac     1275
Arg Val Leu Tyr Gly Pro Arg Leu Asp Glu Arg Asp Cys Pro Gly Asn
    365                 370                 375 tgg acg tgg cca gaa aat tcc cag cag act cca atg tgc cag gct tgg     1323
Trp Thr Trp Pro Glu Asn Ser Gln Gln Thr Pro Met Cys Gln Ala Trp
380                 385                 390                 395 ggg aac cca ttg ccc gag ctc aag tgt cta aag gat ggc act ttc cca     1371
Gly Asn Pro Leu Pro Glu Leu Lys Cys Leu Lys Asp Gly Thr Phe Pro
                400                 405                 410
```

```
ctg ccc atc ggg gaa tca gtg act gtc act cga gat ctt gag ggc acc        1419
Leu Pro Ile Gly Glu Ser Val Thr Val Thr Arg Asp Leu Glu Gly Thr
            415                 420                 425 tac ctc tgt cgg gcc agg agc act caa ggg gag gtc acc cgc gag gtg        1467
Tyr Leu Cys Arg Ala Arg Ser Thr Gln Gly Glu Val Thr Arg Glu Val
            430                 435                 440 acc gtg aat gtg ctc tcc ccc cgg tat gag att gtc atc atc act gtg        1515
Thr Val Asn Val Leu Ser Pro Arg Tyr Glu Ile Val Ile Ile Thr Val
            445                 450                 455 gta gca gcc gca gtc ata atg ggc act gca ggc ctc agc acg tac ctc        1563
Val Ala Ala Ala Val Ile Met Gly Thr Ala Gly Leu Ser Thr Tyr Leu
460                 465                 470                 475 tat aac cgc cag cgg aag atc aag aaa tac aga cta caa cag gcc caa        1611
Tyr Asn Arg Gln Arg Lys Ile Lys Lys Tyr Arg Leu Gln Gln Ala Gln
                480                 485                 490 aaa ggg acc ccc atg aaa ccg aac aca caa gcc acg cct ccc                1653
Lys Gly Thr Pro Met Lys Pro Asn Thr Gln Ala Thr Pro Pro
                495                 500                 505 tga                                                                    1656

(2) INFORMATION FOR SEQ ID NO:3:

(i) SEQUENCE CHARACTERISTICS:
        (A) LENGTH: 31
        (B) TYPE: nucleic acid
        (C) STRANDEDNESS: single
        (D) TOPOLOGY: linear (ii) MOLECULE TYPE: other nucleic acid (iii) HYPOTHETICAL: no (iv) ANTI-SENSE: no (ix) FEATURE:
        (A) NAME/KEY: PCR 5.1 (5' PCR primer)
        (B) LOCATION: 5' end of ICAM-1 coding sequence
        (D) OTHER INFORMATION: bp 1 = G; bp 2-7 = EcoRI
            site; bp 8-31 = 24 bases coding for the
            first eight amino acid residues of hICAM-1

(x) PUBLICATION INFORMATION:
        (A) AUTHORS: Greve, J.M., G. Davis, A.M. Meyer,
            C.P. Forte, S.C. Yost, C.W. Marlor, M.E.
            Kamarck, and A. McClelland
        (B) TITLE: The Major Human Rhinovirus Receptor
            is ICAM-1
        (C) JOURNAL: Cell
        (D) VOLUME: 56
        (F) PAGES: 839-847
        (G) DATE: March 10, 1989
        (K) RELEVANT RESIDUES IN SEQ ID NO:3: From 1 to
            31

(xi) SEQUENCE DESCRIPTION: SEQ ID NO:3:

GGAATTC ATG GCT CCC AGC AGC CCC CGG CCC                                31
        Met Ala Pro Ser Ser Pro Arg Pro
                     5

(2) INFORMATION FOR SEQ ID NO:4:

(i) SEQUENCE CHARACTERISTICS:
        (A) LENGTH: 31 bp
        (B) TYPE: nucleic acid
        (C) STRANDEDNESS: single
        (D) TOPOLOGY: linear (ii) MOLECULE TYPE: other nucleic acid
```

(iii) HYPOTHETICAL: no (iv) ANTI-SENSE: yes (ix) FEATURE:
              (A) NAME/KEY: PCR 3.1 (3' PCR primer)
              (B) LOCATION: 3' end of ICAM-1 coding sequence
              (D) OTHER INFORMATION: bp 1 = G; bp 2-7 = EcoRI
                  site; bp 8-31 = 24 bases complementary to
                  nucleic acid sequence coding for last 8
                  amino acid residues of hICAM-1

(x) PUBLICATION INFORMATION:
              (A) AUTHORS: Greve, J.M., G. Davis, A.M. Meyer,
                  C.P. Forte, S.C. Yost, C.W. Marlor, M.E.
                  Kamarck, and A. McClelland
              (B) TITLE: The Major Human Rhinovirus Receptor
                  is ICAM-1
              (C) JOURNAL: Cell
              (D) VOLUME: 56
              (F) PAGES: 839-847
              (G) DATE: March 10, 1989
              (K) RELEVANT RESIDUES IN SEQ ID NO:4: From 1 to
                  31

(xi) SEQUENCE DESCRIPTION: SEQ ID NO:4:

GGAATTCTCA GGGAGGCGTG GCTTGTGTGT T                                31

(2) INFORMATION FOR SEQ ID NO:5:

(i) SEQUENCE CHARACTERISTICS:
              (A) LENGTH: 47 bp
              (B) TYPE: nucleic acid
              (C) STRANDEDNESS: single
              (D) TOPOLOGY: linear (ii) MOLECULE TYPE: other nucleic acid (iii) HYPOTHETICAL: no (iv) ANTI-SENSE: yes (ix) FEATURE:
              (A) NAME/KEY: ICAM1 probe
              (D) OTHER INFORMATION: complementary to
                  nucleotides 565 to 611 of ICAM-1

(x) PUBLICATION INFORMATION:
              (A) AUTHORS: Greve, J.M., G. Davis, A.M. Meyer,
                  C.P. Forte, S.C. Yost, C.W. Marlor, M.E.
                  Kamarck, and A. McClelland
              (B) TITLE: The Major Human Rhinovirus Receptor
                  is ICAM-1
              (C) JOURNAL: Cell
              (D) VOLUME: 56
              (F) PAGES: 839-847
              (G) DATE: March 10, 1989
              (K) RELEVANT RESIDUES IN SEQ ID NO:5: From 1 to
                  47

(xi) SEQUENCE DESCRIPTION: SEQ ID NO:5:

GAGGTGTTCT CAAACAGCTC CAGCCCTTGG GGCCGCAGGT CCAGTTC                47

(2) INFORMATION FOR SEQ ID NO:6:

(i) SEQUENCE CHARACTERISTICS:
              (A) LENGTH: 47 bp
              (B) TYPE: nucleic acid
              (C) STRANDEDNESS: single
              (D) TOPOLOGY: linear (ii) MOLECULE TYPE: other nucleic acid (iii) HYPOTHETICAL: no

```
            (iv) ANTI-SENSE: yes (ix) FEATURE:
                 (A) NAME/KEY: ICAM3 probe
                 (B) LOCATION: complementary to nucleotides 659
                     to 705 of human ICAM-1

(xi) SEQUENCE DESCRIPTION: SEQ ID NO:6:

CGCTGGCAGG ACAAAGGTCT GGAGCTGGTA GGGGGCCGAG GTGTTCT                    47

(2) INFORMATION FOR SEQ ID NO:7:

(i) SEQUENCE CHARACTERISTICS:
                (A) LENGTH: 49 bp
                (B) TYPE: nucleic acid
                (C) STRANDEDNESS: single
                (D) TOPOLOGY: linear (ii) MOLECULE TYPE: other nucleic acid (iii) HYPOTHETICAL: no (iv) ANTI-SENSE: no (ix) FEATURE:
                 (A) NAME/KEY: PCR 5.5
                 (D) OTHER INFORMATION: bp 1 = G; bp 2-7 = EcoRI
                     site; bp 8-13 = HindIII site; bp 14-25 =
                     hICAM-1 5' untranslated region; bp 26-49 =
                     sequence coding for first 8 amino acid
                     residues of hICAM-1

(x) PUBLICATION INFORMATION:
                 (A) AUTHORS: Greve, J.M., C.P. Forte, C.W.
                     Marlor, A.M. Meyer, H. Hoover-Litty, D.
                     Wunderlich, and A. McClelland
                 (B) TITLE: "Mechanisms of Receptor-mediated
                     Rhinovirus Neutralization Defined by Two
                     Soluble Forms of ICAM-1"
                 (C) JOURNAL: Journal of Virology
                 (D) VOLUME: 65
                 (E) ISSUE: 11
                 (F) PAGES: 6015-6023
                 (G) DATE: 1991
                 (K) RELEVANT RESIDUES IN SEQ ID NO:7: From 1 to
                     49

(xi) SEQUENCE DESCRIPTION: SEQ ID NO:7:

GGAATTCAAG CTTCTCAGCC TCGCT ATG GCT CCC AGC AGC CCC CGG CCC           49
                             Met Ala Pro Ser Ser Pro Arg Pro
                                                  5

(2) INFORMATION FOR SEQ ID NO:8:

(i) SEQUENCE CHARACTERISTICS:
                (A) LENGTH: 40 bp
                (B) TYPE: nucleic acid
                (C) STRANDEDNESS: single
                (D) TOPOLOGY: linear (ii) MOLECULE TYPE: other nucleic acid (iii) HYPOTHETICAL: no (iv) ANTI-SENSE: yes (ix) FEATURE:
                 (A) NAME/KEY: PCR 3.3
                 (D) OTHER INFORMATION: bp 1 = G; bp 2-7 = EcoRI
                     site; bp 8-13 = PstI site; bp 14-16 = stop
                     codon; bp 17-40 = complementary to
                     nucleotide sequence coding for residues 453-446 of
                     hICAM-1

(x) PUBLICATION INFORMATION:
```

(A) AUTHORS: Greve, J.M., C.P. Forte, C.W.
    Marlor, A.M. Meyer, H. Hoover-Litty, D.
    Wunderlich, and A. McClelland
(B) TITLE: Mechanisms of Receptor-mediated
    Rhinovirus Neutralization Defined by Two
    Soluble Forms of ICAM-1
(C) JOURNAL: Journal of Virology
(D) VOLUME: 65
(E) ISSUE: 11
(F) PAGES: 6015-6023
(G) DATE: 1991
(K) RELEVANT RESIDUES IN SEQ ID NO:8: From 1 to
    40

(xi) SEQUENCE DESCRIPTION: SEQ ID NO:8:

GGAATTCCTG CAGTCACTCA TACCGGGGGG AGAGCACATT         40

(2) INFORMATION FOR SEQ ID NO:9:

(i) SEQUENCE CHARACTERISTICS:
       (A) LENGTH: 39 bp
       (B) TYPE: nucleic acid
       (C) STRANDEDNESS: single
       (D) TOPOLOGY: linear (ii) MOLECULE TYPE: other nucleic acid (iii) HYPOTHETICAL: no (iv) ANTI-SENSE: yes (ix) FEATURE:
       (A) NAME/KEY: PCR 3.10
       (D) OTHER INFORMATION: bp 1 = T; bp 2-7 = Xba
           site; bp 8-13 = Bam site; bp 14-16 = stop
           codon; bp 17-39 = sequence complementary to
           nucleotides 693-671 which code for amino
           acid residues 185-178 of hICAM-1

(x) PUBLICATION INFORMATION:
       (A) AUTHORS: Greve, J.M., C.P. Forte, C.W.
           Marlor, A.M. Meyer, H. Hoover-Litty, D.
           Wunderlich, and A. McClelland
       (B) TITLE: Mechanisms of Receptor-mediated
           Rhinovirus Neutralization Defined by Two
           Soluble Forms of ICAM-1
       (C) JOURNAL: Journal of Virology
       (D) VOLUME: 65
       (E) ISSUE: 11
       (F) PAGES: 6015-6023
       (G) DATE: 1991
       (K) RELEVANT RESIDUES IN SEQ ID NO:9: From 1 to
           39

(xi) SEQUENCE DESCRIPTION: SEQ ID NO:9:

TTCTAGAGGA TCCTCAAAAG GTCTGGAGCT GGTAGGGGG          39

(2) INFORMATION FOR SEQ ID NO:10:

(i) SEQUENCE CHARACTERISTICS:
       (A) LENGTH: 43 bp
       (B) TYPE: nucleic acid
       (C) STRANDEDNESS: single
       (D) TOPOLOGY: linear (ii) MOLECULE TYPE: other nucleic acid (iii) HYPOTHETICAL: no (iv) ANTI-SENSE: yes (ix) FEATURE:
       (A) NAME/KEY: PCR 3.19
       (D) OTHER INFORMATION: bp 1 = T; bp 2-7 = Xba
           site; bp 8-13 = Bam site; bp 14-16 = stop -continued

```
              codon; bp 17-19 = lysine codon; bp 20 - 43 =
              sequence complementary to nucleotides coding
              for amino acid residues 453-446 of hICAM-1

(xi) SEQUENCE DESCRIPTION: SEQ ID NO:10:

TTCTAGAGGA TCCTCACTTC TCATACCGGG GGGAGAGCAC ATT                       43

(2) INFORMATION FOR SEQ ID NO:11:

(i) SEQUENCE CHARACTERISTICS:
          (A) LENGTH: 43 bp
          (B) TYPE: nucleic acid
          (C) STRANDEDNESS: single
          (D) TOPOLOGY: linear (ii) MOLECULE TYPE: other nucleic acid (iii) HYPOTHETICAL: no (iv) ANTI-SENSE: yes (ix) FEATURE:
          (A) NAME/KEY: PCR 3.20
          (D) OTHER INFORMATION: bp 1 = T; bp 2-7 = Xba
              site; bp 8-13 = Bam site; bp 14-16 = stop
              codon; bp 17-19 = lysine codon; bp 20 - 43 =
              sequence complementary to nucleotides coding
              for amino acid residues 185-178 of hICAM-1

(xi) SEQUENCE DESCRIPTION: SEQ ID NO:11:

TTCTAGAGGA TCCTCACTTA AAGGTCTGGA GCTGGTAGGG GGC                       43
```

MULTIMERIC ANTIVIRAL AGENT

This application is a continuation of application U.S. Ser. No. 08/159,076 filed Nov. 29, 1993, now abandoned, which is a continuation of U.S. Ser. No. 07/977,589 filed Nov. 17, 1992, abandoned, which is a continuation of U.S. Ser. No. 07/556,238 filed Jul. 20, 1990, abandoned.

BACKGROUND OF THE INVENTION

The present invention relates to novel multimeric configurations and forms of intercellular adhesion molecule (ICAM), including both full length and truncated forms of these proteins, that effectively bind to human rhinovirus and can effectively reduce HRV infectivity.

Full length ICAM, also known as human rhinovirus receptor (HRR), is termed transmembrane ICAM (tmICAM-1); non-transmembrane ICAM forms, also known as truncated ICAM (tICAM), are less than full length. When in a multimeric configuration, preferably as dimers, these proteins display enhanced binding of human rhinovirus (HRV) and are able to reduce HRV infectivity. In addition, these multimerized proteins may also be used to reduce infectivity of other viruses that are known to bind to the 'major' group human rhinovirus receptor (HRR), such as coxsackie A virus, and may also be used to block transmembrane intracellular adhesion molecule (tmICAM) interaction with lymphocyte function-associated antigen-1 (LFA-1) critical to many cell adhesion processes involved in the immunological response. Lastly, these multimerized proteins may be used to study the ICAM-1/HRV interaction especially with respect to designing other drugs directed at affecting this interaction.

Human rhinoviruses are the major causative agent of the common cold. They belong to the picornavirus family and can be classified based on the host cell receptor to which they bind. Tomassini, et al., J. Virol., 58: 290 (1986) reported the isolation of a receptor protein involved in the cell attachment of human rhinovirus. Approximately 90% of the more than 115 serotypes of rhinoviruses, as well as several types of coxsackie A virus, bind to a single common receptor termed the "major" human rhinovirus receptor (HRR); the remaining 10% bind to one or more other cell receptors.

Recently, Greve, J. et al., Cell, 56:839 (1989), co-authored by the co-inventors herein, identified the major HRR as a glycoprotein with an apparent molecular mass of 95,000 daltons and having an amino acid sequence essentially identical to that deduced from the nucleotide sequence of a previously described cell surface protein named intercellular adhesion molecule (ICAM-1). Simmons, D. et al., Nature, 331:624 (1988). Staunton, et al., Cell, 52:925–933 (1988). Subsequently, Staunton, D. E., et al., Cell, 56:849 (1989), confirmed that ICAM-1 is the major surface receptor for HRV. See also, Staunton, et al., Cell, 61:243–254 (1990).

ICAM-1 (number according to Staunton et al., 1988) is an integral membrane protein 505 amino acids long [SEQ ID NO: 1, encoded by nucleotides 138–1653 of SEQ ID NO:2] and has: i) five immunoglobulin-like extracellular domains at the amino-terminal end (amino acid residues 1–453), ii) a hydrophobic transmembrane domain (454–477), and iii) a short cytoplasmic domain at the carboxy-terminal end (478–505). ICAM-1 is a member of the immunoglobulin supergene family and functions as a ligand for the leukocyte molecule, lymphocyte function associated molecule-1 (LFA-1), a member of the integrin family. Heterotypic binding of LFA-1 to ICAM-1 mediates cellular adhesion of diverse cell types and is important in a broad range of immune interactions; induction of ICAM-1 expression by cytokines during the inflammatory response may regulate leukocyte localization to inflammatory sites. The primary structure of ICAM-1 has been found to be homologous to two cellular adhesion molecules, i.e., neural cell adhesion molecule (NCAM) and mylein-associated glycoprotein (MAG).

Several approaches to decreasing infectivity of viruses in general, and of rhinovirus in particular, have been pursued including: i) developing antibody to the cell surface receptor for use in blocking viral binding to the cell, ii) using interferon to promote an anti-viral state in host cells; iii) developing various agents to inhibit viral replication; iv) developing antibodies to viral capsid proteins/peptides; and v) blocking viral infection with isolated cell surface receptor protein, that specifically blocks the viral binding domain of the cell surface receptor.

Using this latter approach, Greve, et al., Cell, 56:879 (1989), supra, reported that purified tmICAM-1 could bind to rhinovirus HRV3 in vitro. Unpublished results with HRV2, HRV3, and HRV14 demonstrate a positive correlation between the ability to bind to rhinovirus and the ability to neutralize rhinovirus particularly if the binding studies are carried out under conditions where ICAM-1 is presented in a particular form and configuration as discussed further, infra. Results (unpublished) using HRV14 and HRV2 demonstrate a positive correlation between the receptor class of the virus and the ability to bind to tmICAM-1 in vitro. That is, ICAM-1, being the major receptor, can bind to HRV3, HRV4, and other "major" receptor serotypes and neutralize them, while it does not bind or neutralize HRV2, a "minor" receptor serotype. Further studies (unpublished), using purified tmICAM-1, demonstrate that it effectively inhibits rhinovirus infectivity in a plaque-reduction assay when the rhinovirus is pretreated with tmICAM-1 (50% reduction of titer at 10 nM receptor and one log reduction of titer at 100 nM receptor protein). These data were consistent with the affinity of rhinovirus for ICAM-1 of Hela cells, which had an apparent dissociation constant of 10 nM, and indicated a direct relationship between the ability of the receptor to bind to the virus and to neutralize the virus.

Because large-scale production of tmICAM-1 is not presently economically feasible, and because maintenance of tmICAM-1 in an active form requires the use of detergents, alternate means of producing a receptor protein for use as a rhinovirus inhibitor are desirable. Forms of the tmICAM-1 cDNA gene have been developed (as well as cell lines that produce the expression products; U.S. Ser. No. 390,662, now abandoned) that have been genetically altered to produce truncated ICAM-1 molecules. These truncated forms of ICAM-1 (tICAM(453) and tICAM(185)) lack the transmembrane region and are secreted into the cell culture medium. They bind to rhinovirus in the assay described in Greve, et al., Cell, 56:879 (1989), supra, although at substantially reduced levels relative to tmICAM-1. Thus, their effectiveness as inhibitors of rhinoviral infectivity appeared to be less than that of tmICAM-1. See generally co-pending applications, U.S. Ser. No. 130,378, now abandoned; U.S. Ser. No. 262,570; U.S. Ser. No. 262,428, now abandoned; U.S. Ser. No. 239,571, now abandoned; and U.S. Ser. No. 390,662, now abandoned.

U.S. Ser. No. 239,571 filed Sep. 1, 1988 and its CIP applications U.S. Ser. No. 262,428, now abandoned and U.S. Ser. No. 390,662, now abandoned are directed to the use of transmembrane rhinovirus receptor as an inhibitor of rhinovirus infectivity using non-ionic detergent to maintain the transmembrane protein in solution and directed to truncated intercellular adhesion molecules (tICAM) having extracellular domains 1, 2, 3, 4, and 5 of transmembrane intercellular adhesion molecules (tmICAM) and which truncated forms do not require the presence of non-ionic detergent for solubilization;

U.S. Ser. No. 130,378 filed Dec. 8, 1987 and its CIP application U.S. Ser. No. 262,570, now abandoned are directed to transfected cell lines which express the major rhinovirur receptor (HRR) and to the indentification of HRR as intercellular adhesion molecule; and U.S. Ser. No. 301,192, now U.S. Pat. No. 5,235,049 filed Jan. 24, 1989 and its CIP application U.S. Ser. No. 449,356, abandoned are directed to a naturally occurring soluble ICAM (sICAM) related to but distinct from tmICAM in that this sICAM lacks the amino acids spanning the transmembrane region and the cytoplasmic region; in addition this sICAM has a novel sequence of 11 amino acids at the C-terminus.

Subsequently, Marlin, S.D., et al., *Nature,* 344:70 (1990), reported the construction and purification of a truncated soluble form of the normally membrane bound ICAM-1 molecule which they termed sICAM-1. It has both the transmembrane domain and the cytoplasmic domain of the protein deleted and differs from the wild-type amino acid sequence by a single conservative substitution at its carboxyl end. It is composed of residues 1–452 of ICAM-1 and of a novel phenylalanine residue at the C-terminus. These workers demonstrated that sICAM-1 was required at levels >50 µg/ml to prevent the binding of HRV14 virus to cells. However, they also found that sICAM-1 at 1 µg/ml (18 nM), when continually present in the culture medium, was able to inhibit by 50% the progression of an infection by HRV54. The inhibitory activity was correlated with the receptor class of the virus, in that coxsackie A13 but not poliovirus or HRV2 was inhibited; infectivity data for HRV14 was not reported, however. Thus, they did not demonstrate a direct correlation between binding and inhibition of infectivity. Further, as discussed in greater detail, infra, attempts to reproduce the results obtained by Marlin, et al. have not been successful and have suggested that a higher concentration of the truncated form of ICAM (10-fold higher than transmembrane ICAM) is required to produce a 50% reduction in viral titer.

To date, no one has been able to demonstrate an agent that binds to and effectively reduces infectivity of human rhinovirus (by blocking viral infection with isolated cell surface receptor protein) as effectively as tmICAM-1; accordingly there continues to exist a need in the art for a form of ICAM-1 that can effectively bind to human rhinovirus and can effectively reduce HRV infectivity.

BRIEF SUMMARY OF THE INVENTION

Provided by the invention are multimeric configurations of transmembrane ICAM (tmICAM-1) as well as multimeric configurations of non-transmembrane ICAM (tICAM). Non-transmembrane ICAM is also known as truncated ICAM, i.e, ICAM substantially without the carboxyl intracellular domain and without the hydrophobic membrane domain and includes but is not limited to the forms of tICAM(453) and tICAM(185). Non-transmembrane forms of ICAM can include functional derivatives of ICAM and mutein forms of tICAM to facilitate coupling. When the truncated ICAM forms are in a multimeric configuration, preferably as dimers, they display enhanced binding of human rhinovirus and are able to reduce viral infectivity. The different forms of ICAM, transmembrane and non-transmembrane, can be multimerized by adsorption to a support. This support can be made of materials such as nitrocellulose, PVDF, DEAE, lipid polymers, as well as amino dextran, or a variety of inert polymers that can adsorb or can be coupled to tICAM, either with or without a spacer or linker.

Multimeric ICAM can also be multimerized by coupling the ICAM to for example, an antibody, a protein carrier, or a cross-linking reagent. An example of an antibody includes anti-ICAM antibody, CL 203; suitable protein carriers include albumin and proteoglycans; and suitable cross-linking reagents include heterobifunctional and homobifunctional cross-linking reagents such as bifunctional N-hydroxysuccinimide esters, imidoesters, or bis-maleimidohexanes. To facilitate coupling, the ICAM can be modified at either the carboxyl end or the the amino end with a reactive amino acid residue such as lysine, cysteine, or other amino acid residue(s) that provide a site(s) to facilitate coupling. These types of modified ICAM are referred to as muteins. In addition, the ICAM can be modified at either termini to comprise a lipid capable of promoting formation of oligomer micelles. The ICAM comprising the multimeric ICAM can be either fully glycosylated, partially glycosylated, or non-glycosylated.

Also provided by the invention are methods for enhancing binding of ICAM and functional derivatives thereof to a ligand, i.e., human rhinovirus, and "major" group receptor viruses, lymphocyte function-associated antigen-1 (LFA-1), plasmodium falciparum (malaria) and the like, wherein the ICAM is presented in a form and a configuration to the ligand and wherein the binding of the ICAM to the ligand is enhanced. The ICAM form can either be transmembrane or non-transmembrane (truncated). Truncated ICAM is ICAM substantially without the carboxyl intracellular domain and without the hydrophobic membrane domain. Preferred truncated forms of ICAM include tICAM(453) and tICAM (185). The ICAM can be modified at either the carboxyl terminus or the amino terminus to enhance multimeric ICAM formation. These modifications can include the addition of reactive amino acid residues such as lysine, cysteine, or other amino acid residue(s) that provide a site(s) to facilitate coupling. The nucleotide sequence for the ICA14 of the method can be contained in a vector, such as a plasmid, and the vector can be introduced into a host cell, for example eukaryotic or prokaryotic cells. The preferred eukaryotic cell is a mammalian cell, i.e., Chinese Hamster Ovary cells; the preferred prokaryotic cell is *E. coli.*

The preferred configuration of the ICAM of the method is multimeric, dimeric being most preferred. The multimeric configuration can comprise a first ICAM cross-linked to a second ICAM or can comprise ICAM adsorbed to a support to thereby generate a multimeric configuration. The support can be high molecular weight and substantially inert polymers such as nitrocellulose, PVDF, DEAE, lipid polymers, and amino-dextran, or a variety of polymers that can adsorb and can be coupled to ICAM, either with or without a spacer or linker. The multimeric ICAM can be multimerized by coupling to for example, an antibody, a protein carrier, or a cross-linking reagent. Preferred cross-linking reagents include heterobifunctional and homobifunctional cross-linking reagents such as bifunctional N-hydroxysuccinimide esters, imidoesters, a bis-maleimidohexanes; preferred protein carriers include albumin and proteoglycans; an example of a preferred antibody includes CL 203 and any other antibodies that do not interfere with HRV binding.

Also provided by the invention are novel pharmaceutical compositions comprising a pharmaceutically acceptable solvent, diluent, adjuvant or carrier, and as the active ingredient, an effective amount of a polypeptide characterized by having human rhinovirus binding activity and reduction of virus infectivity.

Other aspects and advantages of the present invention will be apparent upon consideration of the following detailed description thereof which includes numerous illustrative examples of the practice of the invention.

DETAILED DESCRIPTION

As noted, supra, tmICAM-1 isolated from mammalian cells has the capacity to neutralize human rhinoviruses belonging to the major receptor group, but only if maintained in solution with detergent. Certain soluble fragments of ICAM-1 have been found to have a reduced capacity for binding virus and do not reduce infectivity as effectively as tmICAM-1. To date, no one has been able to ascertain the reason for this reduced capacity.

It has been proposed by others that the rhinovirus receptor exists on cells in a pentameric form. Tomassini, J., and Colonno, R., *J. Virol.,* 58:290–295 (1986). However, quantitation (unpublished results of the co-inventors herein) of the rhinovirus and anti-ICAM-1 monoclonal antibody binding to Hela cells has revealed a maximum of 30,000 virions bound per cell (determined by the binding of $^{35}S$ methionine-labeled HRV) and 50,000-60,000 ICAM-1 molecules per cell (determined by the binding of radio-labeled Mab to ICAM-1). These results prompted further studies to examine the possibility that rather than five, only between 1 and 2 ICAM-1 molecules on the surface of cells are bound per HRV particle bound to the cell.

Genetically engineered forms of truncated ICAM-1 that lack the C-terminal transmembrane domain and that are secreted into the culture medium of mammalian cells transfected with the recombinant gene. The purification of two of these secreted ICAM molecules, tICAM(453) and tICAM (185), from spent culture medium of cells stably transfected with the genes therefor, is described below. In a solution-HRV binding assay and in an HRV neutralization assay, it was found that tICAM(453) has substantially reduced (approximately 200fold) avidity for HRV relative to tmICAM-1. However, when either tmICAM-1 or tICAM (453) or tICAM(185) is first adsorbed to any one of a number of insoluble supports, such as nitrocellulose, PVDF (polyvinylidene difluoride), or DEAE (diethylaminoethyl) membranes, and then incubated with radioactive HRV, the virus-binding activity of tICAM(453) becomes comparable to that of tmICAM-1. This binding of multimeric tICAM (453) or of multimeric tICAM(185) to HRV has the same properties as the binding of HRV to ICAM-1 on Hela cells: it is inhibited by anti-ICAM-1 Mabs, it is specific for rhinoviruses of the major receptor group, and has the same temperature dependence as the binding of rhinovirus to cells (i.e., binds well at 37° C. and undetectably at 4° C.).

As used herein, the following abbreviations and terms include, but are not necessarily limited to, the following definitions.

| Abbreviation | Definition |
|---|---|
| ICAM | Intercellular adhesion molecule - may be used to denote both full length (transmembrane) and truncated (non-transmembrane) forms of the protein. |
| ICAM-1 | Intercellular adhesion molecule-1, also known as ICAM, tmICAM-1; denoting the full length transmembrane protein |
| tmICAM-1 | Transmembrane intercellular adhesion molecule-1, also known as human rhinovirus receptor (HRR)-requires e.g., detergent conditions to be solubilized |
| sICAM-1 | A naturally occurring soluble ICAM-1 having both the transmembrane and the cytoplasmic domain of ICAM-1 deleted; amino acids 1-442 plus 11 novel amino acids; distinguishable from Staunton, et al. tICAM453 which consists of amino acids 1-453 with the terminal tyrosine replaced with phenylalanine. |
| tICAM | Truncated intracellular adhesion molecule, also known as non-transmembrane ICAM. |
| tICAM(453) | Truncated form of ICAM - extracellular amino terminal domain of ICAM; having the transmembrane domain and cytoplasmic domain of ICAM-1 deleted; also referred to as sICAM-1 by Marlin, et al. |
| tICAM(185) | Truncated form of ICAM - extracellular amino terminal domain of ICAM having the transmembrane domain and cytoplasmic domain of ICAM-1 deleted. |

"Multimerization" and "multimeric" include, but are not limited to dimerization and dimeric, and include any multimeric configuration of the ICAM-1 molecule, or fragment thereof, that is effective in reducing viral binding and infectivity;

"transmembrane" generally means forms of the ICAM-1 protein molecule which possess a hydrophobic membrane-spanning sequence and which are membrane bound;

"non-transmembrane" generally means soluble forms of the ICAM-1 protein including so-called "truncated" forms of the protein that, rather than being membrane bound, are secreted into the cell culture medium as soluble proteins, as well as "transmembrane" forms that have been solubilized from cell membranes by lysing cells in non-ionic detergent;

"truncated" generally includes any protein form that is less than the full length transmembrane form of ICAM;

"form" is generally used herein to distinguish among full length and partial length ICAM forms; whereas "configuration" is generally used to distinguish among monomeric, dimeric, and multimeric configurations of possible ICAM forms;

all forms and configurations of the ICAM-1 molecule, whether full length or a fragment thereof, including muteins, whether monomeric or multimeric, may be fully or partially glycosylated, or completely unglycosylated, as long as the molecule remains effective in reducing viral binding and infectivity;

"ligand" is generally used herein to include anything capable of binding to at least one of any of the forms and configurations of ICAM and includes, but is not limited to, human rhinovirus, other viruses that bind to the "major" group human rhinovirus receptor, lymphocyte function-associated antigen-1, and plasmodium falciparum (malaria); and "human rhinovirus" generally includes all human serotypes of human rhinovirus as catalogued in Hamparian, V., et al., *Virol.,* 159:191–192 (1987).

The following examples illustrate practice of the invention.

Example 1 relates to growth, purification and assay of rhinoviruses;

Example 2 relates to production and isolation of monoclonal antibodies to ICAM-1;

Example 3 relates to construction of non-transmembrane truncated forms of ICAM cDNA from full length ICAM-1 cDNA;

Example 4 relates to transfection of mammalian-cells and expression of non-transmembrane truncated forms of ICAM cDNA;

Example 5 relates to isolation and purification of non-transmembrane truncated forms of ICAM-1;

Example 6 relates to radioactive labeling of tmICAM-1, tICAM(185), and tICAM(453) and demonstration of retained capacity for binding to monoclonal antibodies;

Example 7 relates to human rhinovirus binding assays of transmembrane and of transmembrane truncated forms of ICAM-1;

Example 8 relates to CL203 IgG antibody-mediated cross-linking of tICAM(453);

Example 9 relates to multimerization of transmembrane and of non-transmembrane truncated forms of ICAM-1;

Example 10 relates to infectivity-neutralization assay of multimeric transmembrane and of multimeric non-transmembrane truncated forms of ICAM-1; and Example 11 relates to use of multimeric forms of transmembrane and truncated forms of ICAM-1, as effective inhibitors of ICAM/FLA-1 interaction.

EXAMPLE 1
Growth, Purification and Assay of Rhinoviruses

Rhinoviruses were grown, purified, and assayed essentially as described in Abraham, G., et al., *J. Virol.*, 51:340 (1984) and Greve, et al., *Cell*, 56:839 (1989). The serotypes chosen for these studies include HRV14, the standard in the field, and HRV3, which has an approximately 10-fold higher affinity for ICAM than does HRV14. HRV2, which binds to the "minor" receptor rather than the "major" receptor, was used as a negative control.

Rhinoviruses HRV2, HRV3, and HRV14 were obtained from the American Type Culture Collection, plaque purified, and isolated from lysates of infected HeLa-S3 cells. Purified rhinovirus was prepared by polyethylene glycol precipitation and sucrose gradient sedimentation. Viral purity was assessed by SDS-PAGE analysis of capsid proteins and by electron microscopy. Infectivity was quantitated by a limiting dilution infectivity assay scoring for cytophathic effect, essentially as described by Minor, P. D., Growth, assay and purification of picornaviruses, In Virology: A Practical Approach, B. W. J. Mahy, ed (Oxford:IRL Press), pp. 25–41.

EXAMPLE 2
Production and Isolation of Monoclonal Antibodies to ICAM-1

BALB/cByJ female mice were immunized by intraperitoneal injection of 107 intact HeLa cells in 0.5 ml of phosphate-buffered saline (PBS) three times at 3 week intervals. Two weeks later the mice were bled and aliquots of serum were tested for protective effects against HRV14 infection of HeLa cells. Positive mice were boosted by a final injection of $10^7$ HeLa cells, and 3 days later spleen cells were fused to P3X63-Ag8.653 myeloma cells (Galfre, et al., *Nature*, 266:550–552 (1977)) to produce a total of approximately 700 hybridoma-containing wells. Each well was tested by incubating $3 \times 10^4$ HeLa cells in 96-well plates with 100 µl of supernatant for 1 hr at 37° C.; the cells were then washed with PBS, and a sufficient amount of HRV14 was added to give complete cytopathic effect in 24–36 hr. Wells that were positive (protected from infection) were scored at 36 hr.

Cells were removed from wells which scored positive in the first screen and cloned by limiting dilution in 96-well microtiter plates. Supernatants from these wells were tested in the cell protection assay and positive wells were again identified. Further clonings were performed until all of the hybridoma containing wells were positive indicating a clonal population had been obtained. Four cloned cell lines, and their corresponding antibodies, were obtained and were designated c78.1A, c78.2A, c78.4A, c78.5A, c92.1A and c92.5A, respectively.

C92.1A was deposited on Nov. 19, 1987 with the American Type Culture Collection, 12301 Parklawn Drive, Rockville, Md. 20852 and was designated HB 9594.

EXAMPLE 3
Construction of Non-Transmembrane Truncated Forms of ICAM cDNA from Full Length ICAM-1 cDNA A. Preparation of ICAM-1 cDNA Randomly primed cDNA was synthesized from poly A+RNA from HE1 cells using an Amersham™ cDNA synthesis kit under conditions recommended by the supplier. PCR amplification was performed using 100 ng of cDNA for 25 cycles using primers PCR 5.1:

(ggaattcATGGCTCCCAGCAGCCCCCGG-
CCC)  [SEQ ID NO:3] and

PCR 3.1: (ggaattcTCAGGGAGGCGTGGCTTGTG-
TGTT)  [SEQ ID NO:6].

Amplification cycles consisted of 94° C. 1 min, 55° C. 2 min, and 72° C. 4 min. The product of the PCR reaction was digested with EcoR1 and cloned with EcoR1 digested phage vector λGT10 (Stratagene™). Recombinant phage clones were screened by plaque hybridization using ICAM-1 specific oligonucleotides:

GAGGTGTTCTCAAACAGCTCCAGCCCT-
TGGGGCCGCAGGTCCAGTTC (ICAM1)  [SEQ ID NO:5]

and

CGCTGGCAGGACAAAGGTCTGGAGCTGG-
TAGGGGGCCGAGGTGTTCT (ICAM3)  [SEQ ID NO:6].

A positive clone designated XHRR4 was selected and purified. The insert was removed by EcoR1 digestion and subcloned into the EcoR1 site of Bluescript KS+. This clone was designated pHRR2. The entire insert was sequenced and found to contain the entire ICAM-1 coding sequence beginning with the initiator ATG codon and ending with the TGA stop codon as specified by the PCR ICAM-1 sequence (Simmons, et al., *Nature*, 331:624 (1988); Staunton, et al., *Cell*, 52:925–933 (1988) [SEQ ID NO:2]) except for a single substitution of A 1462 for G. This same change was identified in several independent clones and thus represents a polymorphism of the ICAM-1 gene.

B. Construction of tICAM-1(453) and tICAM(185)

Modified forms of the ICAM-1 cDNA were created by PCR amplification reactions (Saiki, et al., *Science*, 230:1350–1354 (1985)) using the full length ICAM-1 cDNA clone pHRR-2 as template. The plasmid DNA was digested with EcoR1 to excise the ICAM-1 insert and treated with alkaline phosphatase to prevent re-circularization of the vector in subsequent ligation steps. Ten ng of template DNA was subjected to 10 cycles of PCR amplification using oligonucleotide primers PCR5.5 and PCR3.3 for tICAM-453 and PCR5.5 and 3.10 for tICAM-185 under the following conditions:

| Temperature (° C.) | Time (mins) |
|---|---|
| 94 | 1 |
| 55 | 2 |
| 72 | 1.5 |
| 71 | 4 (final extension) |

PCR5.5 has the sequence:

GGAATTCAAGCTTCTCAGCCTCGCTATG-GCTCCCAGCAGCCCCCGGCCC   [SEQ ID NO:7]

which consists of EcoR1 and HindIII sites, 12bp ICAM-1 5' untranslated sequence, and the first 24 bp encoding the signal peptide.

PCR3.3 has the sequence:

GGAATTCCTGCAGTCACTCATACCGGGGGGAGAGC-ACATT   [SEQ ID NO:8]

which consists of EcoR1 and Pst1 sites, a stop codon, and 24 bp complementary to the bases encoding the last 8 extracellular amino acids of ICAM-1 (residues 446-453).

PCR3.10 has the sequence:

TTCTAGAGGATCCTCAAAAGGTCTGGAGCTGGTA-GGGGG   [SEQ ID NO:9]

which consists of Xba1 and BamH1 sites, a stop codon, and 23 bp complementary to the bases encoding residues 178–185 of ICAM-1.

The PCR reaction products were digested with EcoR1 (tICAM(453)) or EcoR1 and BamH1 (tICAM(185)) and cloned into the polylinker site of Bluescript™ SK+ (Stratagene). Clones containing the desired inserts were verified by restriction analysis and DNA sequencing. The inserts were excised from Bluescript™ by digestion with HindIII and XbaI and inserted into the expression vector CDM8 (Seed, Nature, 239:840 (1987) at the HindIII and XbaI sites. A clone containing the tICAM(453) insert designated pHRR-8.2 and a clone containing the tICAM(185) insert designated pHRR23-13 were selected and subjected to extensive sequence analysis. This verified the existence of the desired stop codons, and the integrity of the selected regions of ICAM-1 coding sequence.

These plasmids were transfected into COS cells using the DEAE-dextran techniques and the cells were cultured 72 hr. before assay. Surface expression was monitored by FACS using indirect immunofluorescence and a monoclonal antibody specific for ICAM-1. Transient expression in COS cells and immunoprecipitation of metabolicaly labelled ($^{35}$S cysteine) cell supernatants with c78.4A Mab (monoclonal antibody) demonstrated the production of soluble ICAM-1 fragments of 45 kd and 80 kd from pHRR23-13 and pHRR8.2, respectively. The preparation of stable Chinese Hamster Ovary cell transfectants is described below in Example 4.

C. Modified Non-glycosylated Transmembrane ICAM-1 Molecules

A modified full length ICAM-1 was made by simultaneous mutagenesis of N-103, N-118, N-156 and N-175 each to Q. This removes all four N-linked glycosylation sites from the extracellular D2 domain of the ICAM-1 molecule. The resultant molecule, referred to as non-glycosylated transmembrane ICAM, was expressed on the surface of COS cells and was able to bind radio-labeled HRV3 at levels comparable to unmodified ICAM-1. This result demonstrated that glycosylation of domain 2 (the first 184 amino acids) is not required for virus binding to ICAM-1.

It is expected that non-transmembrane ICAM can be similarly modified to yield modified non-glycosylated non-transmembrane ICAM-1 molecules.

D. Construction of Genetically Engineered Forms of Non-Transmembrane (Truncated) ICAM-1 Containing Reactive Residues Suitable for Cross-Linking to Form Multimers A molecule consisting of the 453 amino acid extracellular domain of ICAM-1 with the addition of a novel lysine residue at the C-terminus was constructed by PCR modification of the pHRR-2 cDNA as described above. The primers used were PCR5.5 (described, supra) and PCR 3.19 which has the sequence:

TTCTAGAGGATCCTCACTTCTCATAC-CGGGGGGAGAGCACATT   [SEQ ID NO:10]

and consists of XbaI and BamHI sites, a stop codon, a Lys codon, and 24 bases complementary to the sequence encoding amino acid residues 446 to 453. Following cloning into the CDM8 vector, production of tICAM-453K was confirmed by transient expression in COS cells. Stable CHO cell lines were generated by co-transfection with pSV2-DHFR as described previously.

The same strategy was used to add a Lys residue to the C-terminus of tICAM(185) using PCR5.5 and PCR3.20 which has the sequence:

TTCTAGAGGATCCTCACTTAAAGGTCTG-GAGCTGGTAGGGGGC   [SEQ ID NO:11]

and consists of XbaI and BamHI sites, a stop codon, a Lys codon, and 24 bases complementary to the sequence encoding residues 178 to 185. Transient COS cell expression confirmed the production of tICAM-185 and stable CHO cell lines were derived as described previously.

Three modified forms of tICAM(1–452) that each contain an additional Cys residue were constructed by site directed mutagenesis of the full length ICAM-1 cDNA. In each construct a stop codon was introduced by changing E-453 GAG to TAG. The C-terminus is thus Y-452. Residues N-338, T-360, and Q-387 were each separately mutated to Cys using a second site directed mutagenesis. The presence of the desired mutations were confirmed by DNA sequencing.

The residues selected for mutation to Cys were selected based on a computer generated plot of surface probability which predicts surface exposure of these regions. Also, T-360 is in close promimity to N-358 which is a site of potential N-linked glycosylation. Each of the three Cys modifications was expressed and secreted into the medium of transfected COS cells. Examination of the proteins under reducing and non-reducing conditions showed no indication of the presence of dimers. It is anticipated that cross-linking reagents reactive with sulfhydryl groups can be used to cross-link the Cys modified tICAM forms to obtain multimeric forms.

EXAMPLE 4

Transfection of Cells and Expression of Non-Transmembrane Truncated Forms of ICAM cDNA A. Transfection of Eukaryotic Cells Chinese Hamster Ovary (CHO) cells deficient in dihydrofolate reductase (DHFR) were obtained from Cutter Labs (Berkeley, Calif.). The cells were co-transfected with the plasmid pSV2 DHFR which contains the mouse dihydrofolate reductase (DHFR) gene under control of the SV40 promoter, and with tICAM-453, or tICAM-184 constructs in the CDM8 vector (Seed and Aruffo, *PNAS*, 84:3365–3369 (1987)).

Transfections were done using both electroporation and calcium phosphate methods. Bebbington, supra. Transfected DHFR-positive cells were selected by growth on nucleoside-free media, and pools of transfectants were cloned by limiting dilution.

Cell lines that secrete tICAM were identified by testing culture supernatants with a two-site radioimmune assay (RIA) for ICAM using Mabs c78.4A and c78.5A as follows. A monoclonal antibody against one epitope on ICAM (for example, Mab c78.4A) was adsorbed to plastic 96-well plates (Immunlon plates, Dynatech Inc.), excess binding sites on the plates blocked with bovine serum albumin (BSA), and then culture supernatants incubated with the plates. The plates were then washed and incubated with $^{125}$I-Mab (directed against a second epitope on ICAM for example, c78.5A), and, after washing, the amount of bound $^{125}$IgG determined. The concentration of tICAM was determined by comparing RIA data from unknowns against a standard curve of tm-ICAM at known concentrations. Positive clones were expanded and expression of tICAM forms was confirmed by immunoprecipitation of metabolically labeled cell supernatants with Mab c78.4A.

Cell lines CT.2A (tICAM(453)) and CD12.1A (tICAM (185)) were selected for further study and were subjected to gene amplification in methotrexate containing media as described by Bebbington, et al., supra. A clone derived from CT.2A resistant to 100 nM methotrexate and a CD12.1A clone resistant to 1 $\mu$M methotrexate were used for purification of soluble truncated ICAM-1 proteins.

B. Transfection of Prokaryotic Cells

Because glycosylation of the viral binding domain of ICAM is not required to retain viral binding (as demonstrated in Example 3C), it is anticipated that prokaryotic cells, such as *E. coli*, can be successfully transfected to produce functional proteins.

EXAMPLE 5

Isolation and Purification of Non-Transmembrane Truncated Forms of ICAM-1

Monoclonal antibody affinity chromatography with c78.4A-Sepharose™ has been previously described in co-pending U.S. Ser. No. 130,378 and Greve, et al., *Cell,* 56:839-847 (1989). tICAM secreted into serum-containing media required additional purification steps due to the high level of contaminating protein in the serum. Before elution from the Mab-affinity column, the column was washed with 1 M NaCl to remove loosely-bound proteins. For tICAM (453), the partially purified tICAM(453) eluted from the c78.4-Sepharose™ column was dialysed into 10 mM Tris (pH 6.0), absorbed onto a mono-Q™ column (Pharmacia), and eluted with a 0–0.3 M NaCl gradient. tICAM184 was further purified by gel filtration on a Superose-12™ column.

It is also recognized that non-transmembrane truncated forms of ICAM-1 may be purified using standard ion exchange methodology without using monoclonal antibody affinity chromotography.

EXAMPLE 6

Radioactive Labeling of tmICAM-1, tICAM185, and tICAM453 and Demonstration of Retained Capacity for Binding to Monoclonal Antibodies The epitopes reactive with monoclonal antibodies c78.4A and c78.5A are conformationally-dependent epitopes and thus can be used as analytical probes for confirming retention of the native ICAM structure. Known amounts of purified ICAM were incubated with c78.4A or c78.5A IgG-Sepharose™ and the fraction of the radioactivity bound determined. These experiments showed that the purified tmICAM-1, tICAM(185), and tICAM(453) completely retained the ability to bind to these monoclonal antibodies.

Transfectants were metabolically labeled with $^{35}$S cysteine, and cell lysates (for transmembrane ICAM) or culture supernatants (for truncated ICAM) were prepared and incubated with c78.4A IgG-Sepharose™ beads. The beads were washed and adsorbed proteins were eluted with SDS and analysed by SDS-PAGE; see Greve, et al., *Cell,* 56:839–847 (1989)). It was found that the isolated proteins were quantitatively bound to the c78.4A and c78.5A Mabs.

Accordingly, the tICAM(185) and tICAM(453) both have retained native ICAM structure.

EXAMPLE 7

Human Rhinovirus Binding Assays of Transmembrane and of Non-Transmembrane Truncated Forms of ICAM-1

Described below are three binding assays used to assess binding activity of the various forms of ICAM.

A. Pelleting Assay

[$^{35}$S]cysteine-labeled tmICAM-1 or tICAM was mixed with HRV3 in 100 μl of 10 mM HEPES (pH 7.5), 150 mM NaCl, 1 mM $MgCl_2$, 1 mM $CaCl_2$, 0.1% Triton X-100. The mixture was incubated for 30 min. at 37° C., cooled on ice, layered on top of a cushion of 200 μl of 10% glycerol, 0.2 M triethanolamine (pH 7.5), and centrifuged in a Beckman air-driven centrifuge at 134,000×g for 30 min. at 4° C. The top 275 μl was removed, and the pellet was analyzed by SDS-PAGE and scintillation counting. Silver-staining of SDS gels of control experiments indicated that essentially all of the HRV3 is pelleted under these conditions and essentially all of the ICAM remains in the supernatant. The results are shown in Table 1.

TABLE 1

| ICAM | % ICAM Pelleted* |
|---|---|
| tmICAM-1 | 11.6% |
| tICAM(453) | 1.0% |
| tICAM(185) | 4.3% |

*average of 4 experiments; these numbers cannot be directly converted into relative affinities These data show that both truncated forms of ICAM bind to rhinovirus, but at levels substantially reduced relative to that of tmICAM.

B. Solution Binding Assay

To obtain quantitative information on the relative affinity of tmICAM and tICAM fragments in solution, a solution competition assay was developed in which soluble tmICAM or soluble tICAM fragments were used to inhibit the binding of $^{35}$S HRV3 to previously immobilized ICAM-1; nonionic detergent (Triton X-100) was included in the buffers so that the different proteins could be compared under identical conditions. First, tmICAM-1 (isolated in the presence of 0.1% octylglucoside instead of Triton X-100) was diluted 10-fold into a Tris/NaCl buffer and allowed to adsorb to the walls of a microtiter plate (Immunlon-4, Dynatech) overnight. Nonspecific binding sites on the plate were then blocked with 10 mg/ml BSA and binding experiments performed in 0.1% Triton X-100/1 mg/ml BSA/Tris/NaCl. Approximately 20,000 cpm of $^{35}$S HRV3 were mixed with varying amounts of ICAM either tmICAM, tICAM(453) or tICAM(185), incubated for 1 hour at 37° C., and then added to wells of the microtiter plates and incubated for 3 hr at 37° C. The plates were washed and the bound radioactivity determined.

As shown in Table 2, tmICAM-1 inhibits virus binding half-maximally at low concentrations (.008 μM) while tICAM(453) and tICAM(185) inhibit at much higher concentrations (2.8 μM and 7.9 μM, respectively; or 350 to almost 1000 fold higher than tmICAM.

TABLE 2

| ICAM | $IC_{50}$* |
|---|---|
| tmICAM | 8.0 ± 3.3 nM (N = 3) |
| tICAM(453) | 2.8 ± 0.6 μM (N = 3) |
| tICAM(185) | 7.9 ± 2.8 μM (N = 3) |

*$IC_{50}$ is the concentration of soluble ICAM needed to inhibit HRV3 binding by 50%.

These data confirm and extend the earlier observations that tICAM(453) and tICAM(185) do bind to rhinovirus but with lower affinities than does tmICAM-1 and provide evidence that the virus binding site is encompassed within the two N-terminal domain (185 residues) of ICAM-1.

C. Dot-Blot Assay

An alternative method of measuring binding activity was utilized in which tmICAM-1, tICAM(453), or tICAM(185) were adsorbed to nitrocellulose filters, the non-specific binding sites on the filters blocked with 10 mg/ml bovine serum albumin (BSA), and radioactive virus or $^{125}I$ Mab to ICAM-1 incubated with the filter for 60 mins at 37° C. The filters were washed with buffer and the filters exposed to X-ray film.

The amount of radioactivity bound to the filters was determined by densitometry of the autoradiograms, and the data is expressed as HRV3 binding (in arbitrary units) normalized to the amount of ICAM bound to the blot by a parallel determination of the amount of $^{125}$Mab c78.4A or c78.5A bound to the ICAM (bound to the blot). The results are shown in Table 3.

TABLE 3

Binding of $^{35}$S HRV3 to Immobilized ICAM*

| ICAM | tICAM(453) | ratio ICAM/tICAM453 |
|---|---|---|
| 1.2 ± 1.1 | 0.52 ± 0.45 | 2.3 |

*Average of 5 experiments. Data is expressed in arbitrary densitometric units of $^{35}$S HRV3 binding/$^{125}$I anti-ICAM Mab binding.

Additional studies with tICAM 185 have been initiated. Binding experiments have demonstrated equivocal results. It is anticipated that steric hinderance may play a role. The size of the virus is approximately 30 nanometers. The length of tICAM(185) is less than 10 nanometers. The use of a spacer or linker would provide better accessibility for binding.

The results from this experiment indicate that under these assay conditions tICAM(453) is capable of binding rhinovirus at levels comparable to those of tmICAM-1 when the amount of virus bound was normalized to the amount of $^{125}I$ MAb bound. Further, these results indicate that the tICAM forms are capable of binding to rhinovirus, but that the binding avidity is dependent upon the configuration of the tICAM. tmICAM-1 may be a small multimer (probably a dimer) and presentation of tICAM in a multimeric form mimics this multimeric configuration.

Evidence supporting this hypothesis comes from quantitative binding studies (unpublished), in which the ratio of the maximum number of rhinovirus particles and the maximum number of antibody molecules that can be bound to cells is approximately 1.5, as discussed supra. This is in contrast to the earlier work of Tomassini, J., et al., *J. Virol.*, 58:290 (1986), which suggested a complex of five molecules needed for binding. Their conclusion was based on an erroneous interperation of gel filtration data that failed to take into account bound detergent molecules.

EXAMPLE 8

CL203 IgG Antibody-Mediated Cross-Linking of tICAM (453)

To provide additional evidence that the higher relative binding activity of tmICAM-1 is due to a multimeric form of the protein, the tICAM(453) protein was pre-incubated with CL203, a monoclonal antibody to ICAM-1 that does not inhibit virus binding to ICAM-1 and binds to a site C-terminal to residue 184 Staunton, et al., *Cell,* 56:849 (1989) and *Cell,* 61:243 (1990). Thus, the antibody can effectively "cross-link" two molecules of tICAM(453), to create "dimers" of tICAM(453), yet without blocking the virus-binding site on each of the two molecules of tICAM (453). When a mixture of CL203 IgG and tICAM(453) at a 4:1 weight ratio was tested in the competition assay, it was found that the antibody cross-linked tICAM(453) inhibited HRV3 binding at a concentration 7.4-fold lower than tICAM (453) alone consistent with the idea that tmICAM-1 binds with higher affinity to rhinovirus because it is a dimer or a small multimer.

To create alternative multimeric forms of tICAM, several further modified truncated forms of ICAM were constructed as described, supra, in Example 3. These forms can then be multimerized as described in Example 9, below.

EXAMPLE 9

Multimerization of Transmembrane and Non-Transmembrane Truncated Forms of ICAM-1

There are several ways that tICAM can be converted to a multimeric form having enhanced viral binding and neutralization activity over the monomeric form. For example, tICAM(453) can be coupled to an inert polymer, such as amino dextran (MW 40,000) using homobifunctional (such as N-hydroxy succinimide (NHS) esters) or heterobifunctional (such as those containing NHS-ester and photoactivatable or sulfhydryl-reactive groups) cross-linking reagents utilizing the amino group on the amino dextran and an amino or other group on the tICAM. A number of examples of appropriate cross-linking reagents can be found in the Pierce Chemical Company catalog (Rockford, Ill.).

As tICAM is poorly reactive with NHS-ester-based compounds, a tICAM with a genetically engineered C-terminal lysine residue (see Example 3) would have improved coupling efficiency to supports with homobifunctional reagents whereas genetically engineered C-terminal cysteine residues would facilitate coupling by heterobifunctional reagents such as sulfo-maleimidobenzoyl-N-hydroxysuccinimide ester (MBS).

Alternatively, soluble tICAM multimers can be created by genetically engineering reactive residues into the C-terminal end of tICAM. For example, free cysteine residues can be created in relatively hydrophilic sequences in the C-terminal region of tICAM (which would have a greater tendency to be solvent-exposed). It is anticipated that this would allow for the creation of dimers in situ; alternatively, monomers could be purified and dimers created in vitro by disulfide exchange.

Another approach requires the placement of lysine residues at similar positions and cross-linking purified protein in vitro with homobifunctional NHS-esters. Examples of such lysine residues are residues 338, 360, 387.

Crosslinking cysteine residues to each other can be accomplished by reaction of tICAM with free cysteine groups with bis-maleimidohexane (Pierce Chemical Co.) or other bis-maleimido-analogs. Cross-linking free cysteine residues on tICAM to amino groups on carrier molecules can be accomplished by reaction with m-maleimidobenzoyl-N-hydroxysuccinimide ester. Crosslinking amino groups on tICAM molecules can be accomplished with homobifunctional N-hydroxysuccinimide esters (for examples, see Pierce Chemical Co. catalog). Alternatively, the carbohydrate groups on tICAM can be oxidized to aldehydes and coupled to hydrazine-activated amino groups on a carrier molecule.

EXAMPLE 10

Infectivity-Neutralization Assay of Transmembrane and Non-Transmembrane Truncated Forms of ICAM-1

Three different assays for virus infectivity have been used. These different assays take into account the differences in transmembrane ICAM and non-transmembrane solubilities.

A. Plaque-reduction Assay in the Presence of Detergent

The results of this assay indicate what the highest dilution of virus is that will still be effective in killing cells. Virus is pre-incubated with transmembrane ICAM protein in the presence of 0.1% TX100, serially diluted into culture medium, incubated for 30 min with HeLa cells at 106 cells/ml, diluted 10-fold, and plated out into multiple wells of a 96-well microtiter plate having varying dilutions of virus. 0.1% TX100 was used as positive control. After 5 days, the wells are scored as either being infected or not by the presence of cytopathic effect (CPE) and the titer expressed as plaque-forming units/ml (PFU/ml) of the original virus. This assay was described in U.S. Ser. No. 239,571 and was used to demonstrate the antiviral activity of tmICAM-1 (which required the presence of detergent to remain in solution). The concentration of ICAM protein used is the initial concentration in the pre-incubation mixture; however, the ICAM protein is not present continually during the infection in that the protein is serially diluted. While the presence of detergent is required to solubilize the tmICAM, the presence of the detergent does kill cells; thus, the need for the serial dilutions.

B. Plaque-Reduction Assay in the Absence of Detergent

In this plaque-reduction assay, a more traditional assay, HeLa cells are infected with serial dilution of rhinovirus as above, but detergent is not present; thus, this assay cannot be used to assay tmICAM. In this assay the tICAM is present continually in the culture medium at the indicated concentration. tmICAM-1 (which requires the presence of detergent) cannot be assayed in this system because the addition of the required detergent would kill the HeLa cells.

C. Plaque-reduction Assay In Continual Presence of Virus and ICAM

This assay is similar to that utilized by Marlin, et al. (Nature 1990) in which a culture of HeLa cells is infected with 100 PFU of virus in the presence or absence of ICAM protein and cultured approximately 4 days until cytopathic effect (CPE) is apparent. The cultures are then scored for CPE visually. The assay conditions were the same as Marlin, supra. Scoring was done visually rather than by a staining procedure using crystal violet.

In this assay, there is no detergent present, the ICAM is present continually, and this assay measures a reduction in virus replication/propagation at an arbitrary point in time.

The data from these three different assays for virus infectivity is summarized in Table 4.

TABLE 4

| ICAM | Assay: | IC50% ($\mu M$)* | | |
|---|---|---|---|---|
| | | A | B | C |
| tmICAM-1 | | 0.03 | ND | ND |
| tICAM(453) | | >20 | 0.2 | 0.2 |
| tICAM(185) | | >20 | ND | ND |

*IC50% is defined as the concentration of ICAM protein needed to inhibit HRV3 infectivity by 50%.

These data indicate that tmICAM-1 is significantly more active in reducing viral infectivity than the truncated ICAM proteins, even when compared in different assay systems. The differences in neutralization activity of tICAM(453) in assay (A) and assay (B) indicate that the neutralization mediated by tICAM(453) requires the continual presence of tICAM(453) in the culture medium and is reversible. That the neutralization is reversible is indicated by the lack of neutralization observed in assay (A). In contrast, the neutralization activity of tmICAM-1 is >667-fold higher than tICAM(453) and than tICAM(185) in assay (A) and could be even greater in assay (B) if it were possible to have the tmICAM-1 present continually in the culture medium in the absence of detergent.

To compare these results with those of Marlin, et al., an attempt was made to reproduce their assay conditions. As shown in Table 4, there is a good correlation between the results in assay (B) and assay (C), although the IC50% for tICAM(453) is 10-fold greater than that seen by Marlin, et al. To determine if this is due to a difference in the serotype of rhinovirus used, the assay was repeated with HRV14 and HRV54 (the serotype used by Marlin, et al). The IC50% for both of these serotypes was 0.2 $\mu M$ tICAM(453), indicating that there is no difference in serotype sensitivity between HRV14, HRV54, and HRV3.

To attempt to resolve this discrepancy, the same buffers that Marlin, et al. used were used to see if they affected the infectivity of rhinovirus in assay (C). Marlin, et al. prepared their sICAM-1 protein in a buffer containing 50 mM triethanolamine (TEA)/20 mM Tris. When this buffer alone was added to control infections (1/10th volume, final concentration 5 mM TEA/2 mM Tris) of HRV3 and HRV14, virtually complete inhibition of CPE was observed. Thus, it is possible that there could be buffer effects on virus replication unrelated to the presence of any form of ICAM.

EXAMPLE 11

Use of Multimeric Forms of Transmembrane and of Truncated Forms of ICAM-1, as Effective Inhibitors of ICAM/FLA-1 Interaction The normal function of ICAM-1 is to serve as a ligand of the leukocyte integrin LFA-1; interaction between these two molecules leads to adhesion between leukocytes and a variety of other cells. The ability of tICAM(453) to inhibit adhesion between ICAM-1 and LFA-1 on cells was examined as follows. ICAM-1 was adsorbed to microtiter plates as described in Example 7C. JY cells, which express LFA-1, adhere to ICAM-expressing cells or to ICAM-1-coated culture dishes (Staunton, et al., JCB). JY cells were pre-incubated in the presence or absence of tICAM(453) for 30 min at 37° C., and then added to the ICAM-1-coated plates and incubated for 60 min at 37° C. The microtiter plates were then washed and the number of cells attached to the plates were counted.

TABLE 5

Inhibition of LFA-1/ICAM-1 interaction by soluble ICAM

| tICAM(453) (μg/ml) | % control cell binding* |
|---|---|
| — | 100 |
| 100 | 96 |
| 300 | 93 |
| 600 | 75 |

*Binding to ICAM-1-coated microtiter plates; 10 μg/ml anti-LFA-1 or anti-ICAM-1 MAb inhibited binding to >1%.

As can be seen in Table 5, even at high concentrations of tICAM(453) (0.6 mg/ml), minimal inhibition of JY cell binding was observed. This is probably due to the fact that the adhesion between cells is a highly cooperative process involving thousands of molecules and the affinity of tICAM (453) is low. Presentation of tICAM(453) or tICAM(185) in a multimeric configuration would increase the affinity of the tICAM for cells and could serve as an effective anti-adhesive agent in inflammatory or autoimmune diseases.

The foregoing examples describe the creation of soluble, multimeric forms of tICAM that substantially increase tICAM-1 binding and neutralizing activity.

While the present invention has been described in terms of specific methods and compositions, it is understood that variations and modifications will occur to those skilled in the art upon consideration of the present invention.

For example, it is anticipated that smaller protein fragments and peptides derived from ICAM-1 that still contain the virus-binding site would also be effective in a multimeric configuration. It is also anticipated that multimeric ICAM may be effective inhibitors of the ICAM-1/LFA-1 interaction, as the affinity between these two molecules is quite low and the cell-cell binding mediated by these two molecules is highly cooperative.

Although the preferred form and configuration is a non-transmembrane (truncated) ICAM in dimeric configuration, it is not intended to preclude other forms and configurations effective in binding virus and effective in neutralizing viral activity from being included in the scope of the present invention.

Further, it is anticipated that the general method of the invention of preparing soluble protein forms from insoluble, normally membrane bound receptor proteins can be used to prepare soluble multimeric forms of other receptor proteins useful for binding to and decreasing infectivity of viruses other than those that bind to the "major group" receptor. Such other viruses include polio, Herpes Simplex, and Epstein-Barr virus.

Numerous modifications and variations in the invention as described in the above illustrative examples are expected to occur to those skilled in the art and consequently only such limitations as appear in the appended claims should be placed thereon.

Accordingly it is intended in the appended claims to cover all such equivalent variations which come within the scope of the invention as claimed.

What is claimed is:

1. A multimeric antiviral agent comprising two or more monomers selected from the group consisting of monomeric transmembrane intercellular adhesion molecule-1(tmICAM-1) and monomeric fragments of tmICAM-1, with thc proviso that when said multimer is a dimer said monomers cannot both be tmICAM-1, wherein each of said monomers comprises the human rhinovirus (HRV) binding site and retains the ability to bind to HRV and reduce infectivity thereof, and wherein said multimeric antiviral agent mimics the multimeric configuration of tmICAM-1 and exhibits enhanced binding to said HRV relative to at least one of the constituent monomers.

2. A multimeric antiviral agent according to claim 1 wherein at least one of said monomers is selected from the group consisting of truncated intercelluar adhesion molecule-1 (tICAMs).

3. A multimeric antiviral agent according to claim 2 wherein said monomers are selected from the group consisting of tICAM(453) and tICAM(185).

4. A multimeric antiviral agent according to claim 1 wherein each of said monomers contains at least one reactive amino acid.

5. A multimeric antiviral agent according to claim 4, wherein each of said monomers contains at least one lysine residue, wherein each of said monomers is linked to at least one other such monomer via said lysine residues, and wherein said multimeric antiviral agent binds to HRV and reduces infectivity thereof.

6. A multimeric antiviral agent according to claim 4 wherein each of said monomers contains at least one cysteine residue, wherein each of said monomers is linked to at least one other such monomer via a cysteine disulfide linkage, and wherein said multimeric antiviral agent binds to HRV and reduces infectivity thereof.

7. A multimeric antiviral agent according to claim 1 wherein said multimer is a dimer.

8. A method for reducing infectivity of human rhinovirus (HRV), said method comprising contacting said HRV with a multimeric antiviral agent according to claim 1, 2, 3, 4, 5, 6, or 7.

9. A pharmaceutical composition comprising a pharmaceutically acceptable solvent, diluent, adjuvant, or carrier, and a multimeric antiviral agent according to claim 1, 2, 3, 4, 5, 6, or 7.

10. In a method for binding a truncated intercellular adhesion molecule-1 (tICAM) to human rhinovirus (HRV), the improvement comprising presenting said tICAM to said HRV in the form of a multimeric antiviral agent according to claim 1, 2, 3, 4, 5, 6, or 7.

* * * * *